(12) United States Patent
Himawan

(10) Patent No.: US 7,405,276 B2
(45) Date of Patent: Jul. 29, 2008

(54) METHOD OF PRODUCING BISPECIFIC MOLECULES BY PROTEIN TRANS-SPLICING

(75) Inventor: Jeff Himawan, Tampa, FL (US)

(73) Assignee: EluSys Therapeutics, Inc., Pine, Brook, NJ (US)

( * ) Notice: Subject to any disclaimer, the term of this patent is extended or adjusted under 35 U.S.C. 154(b) by 322 days.

(21) Appl. No.: 10/415,840

(22) PCT Filed: Nov. 1, 2001

(86) PCT No.: PCT/US01/45653

§ 371 (c)(1),
(2), (4) Date: Nov. 3, 2003

(87) PCT Pub. No.: WO02/46208

PCT Pub. Date: Jun. 13, 2002

(65) Prior Publication Data

US 2004/0077842 A1    Apr. 22, 2004

Related U.S. Application Data

(60) Provisional application No. 60/244,811, filed on Nov. 1, 2000.

(51) Int. Cl.
*C12P 21/08* (2006.01)
(52) U.S. Cl. ............. 530/387.3; 530/388.2; 530/388.22
(58) Field of Classification Search ............. None
See application file for complete search history.

(56) References Cited

U.S. PATENT DOCUMENTS

| | | | |
|---|---|---|---|
| 4,522,811 A | 6/1985 | Eppstein et al. |
| 4,672,044 A | 6/1987 | Schreiber |
| 4,816,397 A | 3/1989 | Boss et al. |
| 4,816,567 A | 3/1989 | Cabilly et al. |
| 5,223,409 A | 6/1993 | Ladner |
| 5,225,539 A | 7/1993 | Winter et al. |
| 5,470,570 A | 11/1995 | Taylor et al. |
| 5,487,890 A | 1/1996 | Taylor et al. |
| 5,514,548 A | 5/1996 | Krebber et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,653,979 A | 8/1997 | Muzykantov et al. |
| 5,661,016 A | 8/1997 | Lonberg et al. |
| 5,693,762 A | 12/1997 | Queen et al. |
| 5,821,331 A | 10/1998 | Hammond et al. |
| 5,843,440 A | 12/1998 | Pouletty et al. |
| 5,879,679 A | 3/1999 | Taylor et al. |
| 5,914,112 A | 6/1999 | Bednar et al. |
| 5,985,615 A | 11/1999 | Jakobovits et al. |
| 6,054,312 A | 4/2000 | Larocca et al. |
| 6,057,098 A | 5/2000 | Buechler et al. |
| 6,060,596 A | 5/2000 | Lerner et al. |
| 6,488,927 B2 | 12/2002 | Muzykantov et al. |
| 2003/0152563 A1 | 8/2003 | Muzykantov et al. |
| 2004/0053408 A1 | 3/2004 | Muzykantov et al. |

FOREIGN PATENT DOCUMENTS

| | | |
|---|---|---|
| EP | 125023 A1 | 11/1984 |
| EP | 171496 A2 | 2/1986 |
| EP | 171496 A3 | 2/1986 |
| EP | 173494 A2 | 3/1986 |
| EP | 173494 A3 | 3/1986 |
| EP | 184187 A2 | 6/1986 |
| EP | 184187 A3 | 6/1986 |
| GB | 2034323 A | 6/1980 |
| WO | WO 87/02671 | 5/1987 |
| WO | WO 91/17271 | 11/1991 |
| WO | WO 92/01047 | 1/1992 |
| WO | WO-92/05801 A1 | 4/1992 |

(Continued)

OTHER PUBLICATIONS

Scot et al. (1999) Production of cyclic peptides and proteins in vivo. Proc. Natl. Acad. Sci. U S A. vol. 96, No. 24, pp. 13638-13643.*

(Continued)

*Primary Examiner*—David A. Saunders
*Assistant Examiner*—F. Pierre VanderVegt
(74) *Attorney, Agent, or Firm*—Lahive & Cockfield, LLP; Megan E. Williams

(57) ABSTRACT

The invention provides methods of using protein trans-splicing for the production of bispecific molecule which has a first antigen recognition portion that binds a C3b-like receptor and a second antigen recognition portion that binds an antigenic molecule present in the circulatory system of a mammal. The invention also provides bispecific molecules produced by protein trans-splicing. The bispecific molecules of the invention can be used for the clearance of pathogenic antigenic molecules from the circulatory system of a mammal. The invention further provides methods of using protein trans-splicing for the production of polyclonal libraries of bispecific molecules, which comprise populations of bispecific molecules with different antigen recognition specificities. Such polyclonal libraries of bispecific molecules can be used for targeting multiple epitopes of a pathogenic antigenic molecule and/or multiple variants of a pathogenic antigenic molecule.

30 Claims, 7 Drawing Sheets

FOREIGN PATENT DOCUMENTS

Figure 1A:
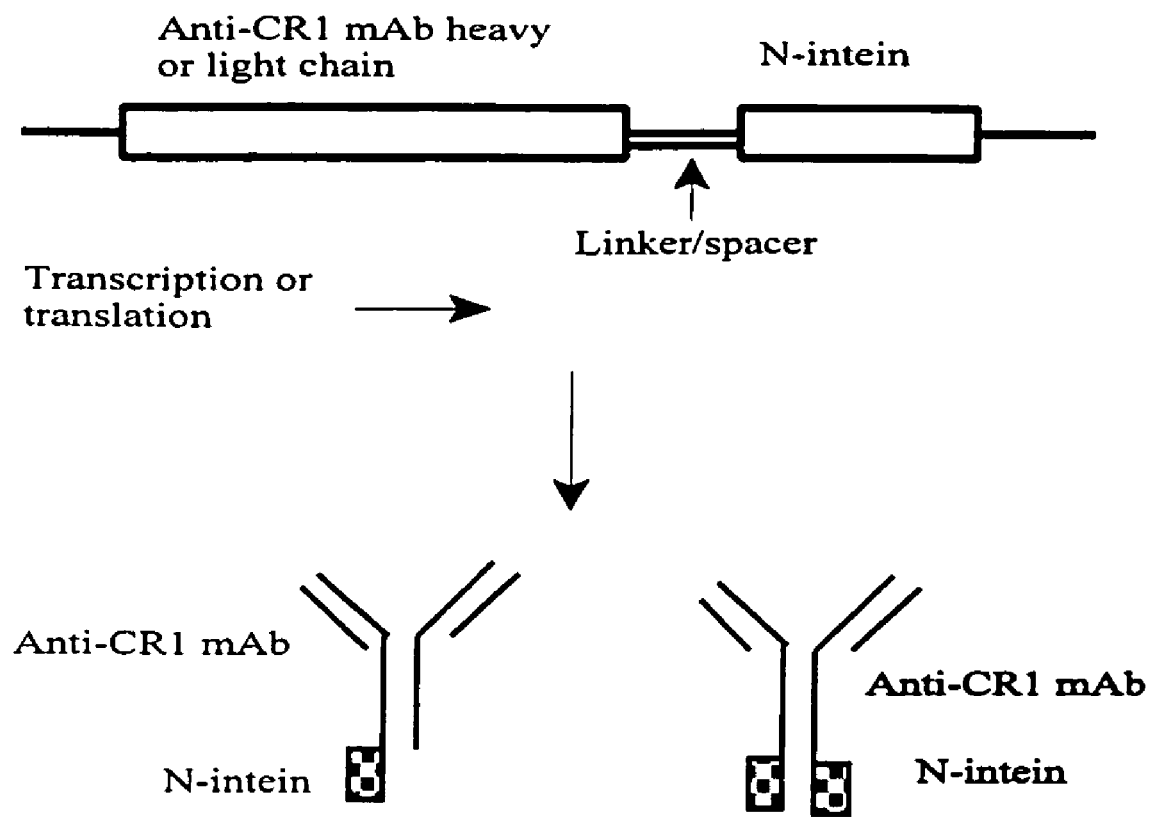
Figure 1C:
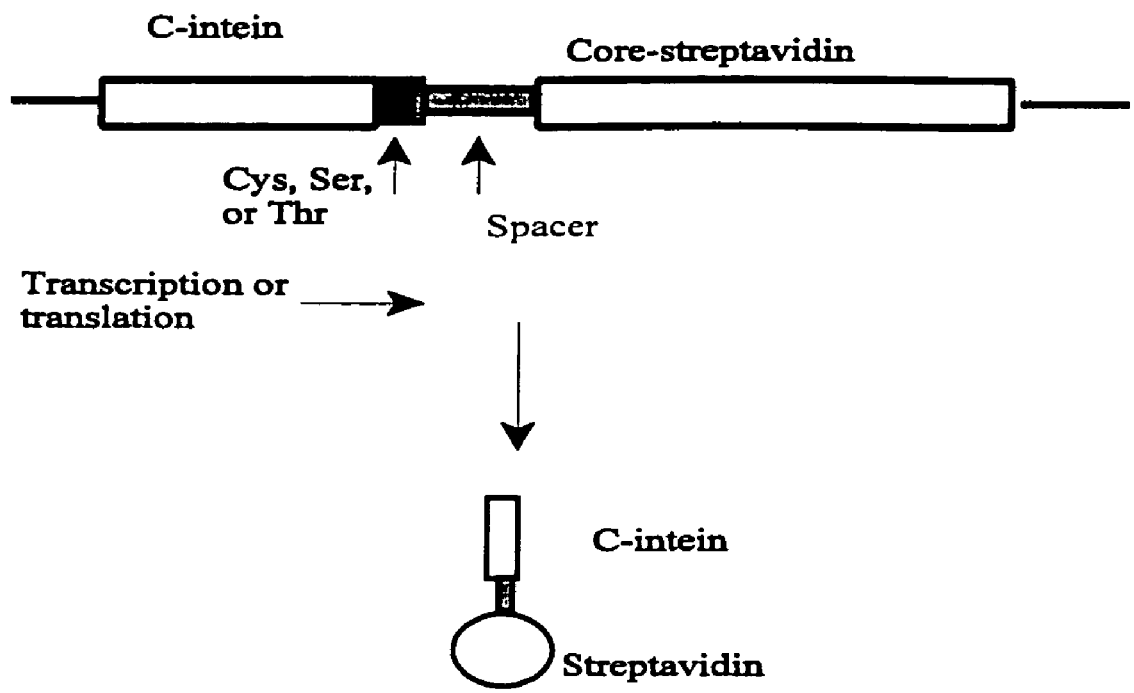
Figure 1D:
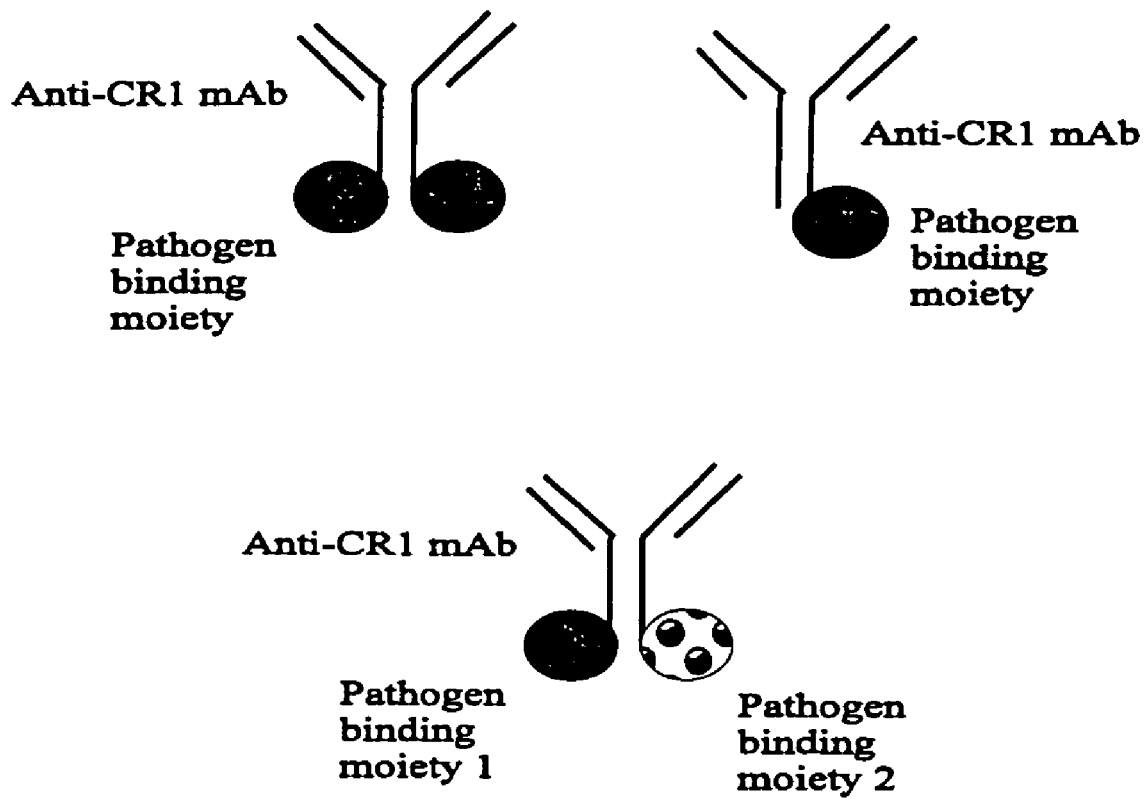
Figure 1E:
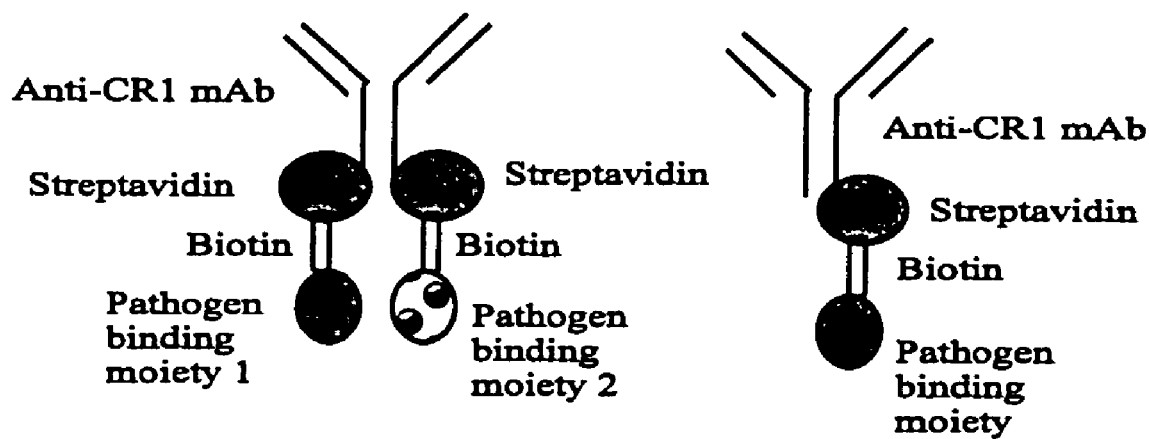
Figure 2:
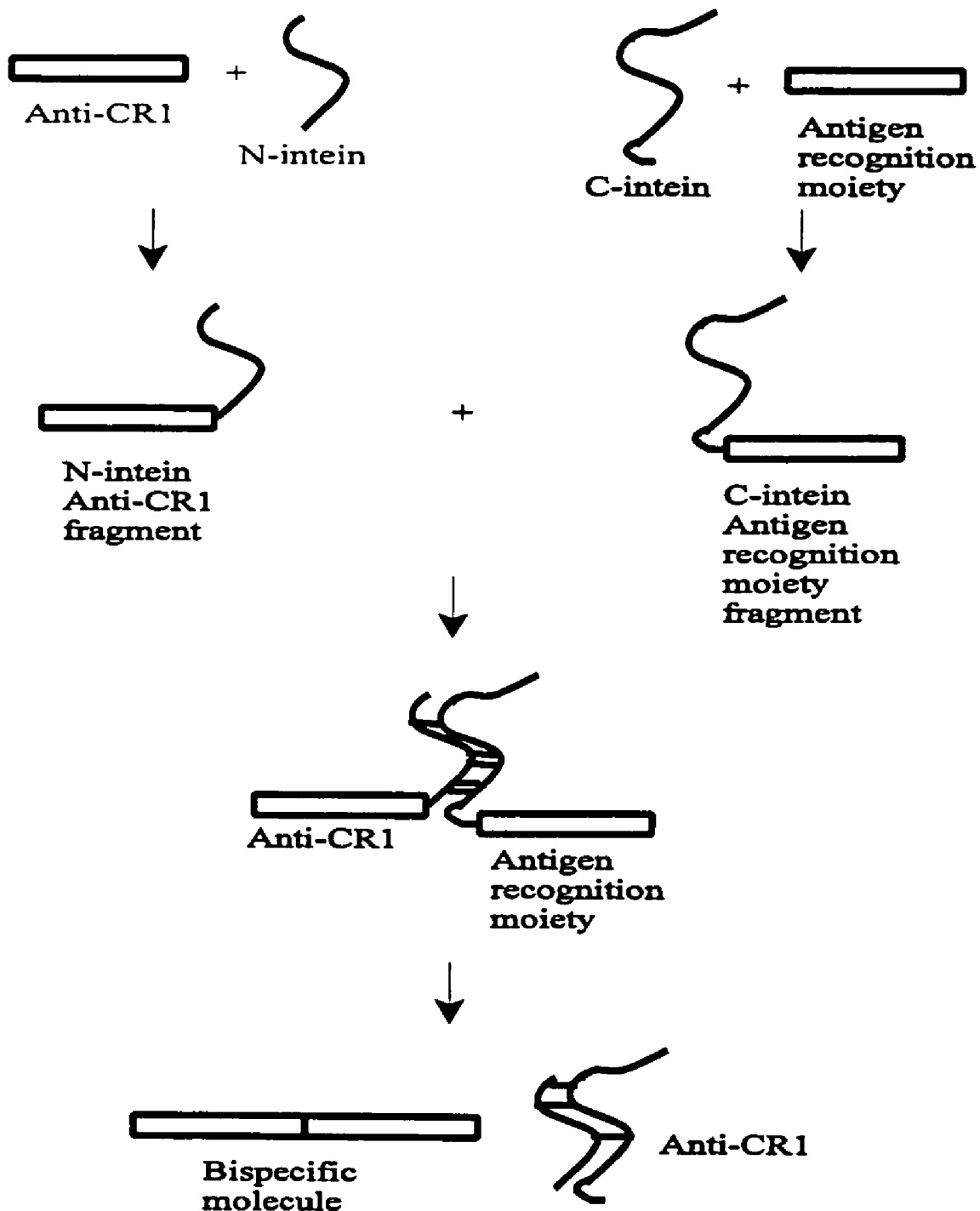

| WO | WO 92/09690 | 6/1992 |
|---|---|---|
| WO | WO 92/15679 | 9/1992 |
| WO | WO 92/18619 | 10/1992 |
| WO | WO 92/20791 | 11/1992 |
| WO | WO 93/01288 | 1/1993 |

OTHER PUBLICATIONS

American Heritage College Dictionary: Third Edition. [1997] Houghton Mifflin Co., Boston. p. 59.*

Cruse, JM et al. Illustrated Dictionary of Immunology [1995], p. 21.*

Air, 1981, "Sequence relationships among the hemagglutinin genes of 12 subtypes of influenza A virus", Proc. Natl. Acad. Sci. USA 78:7639-7643.

Altura and Hershey, 1968, "RES phagocytic function in trauma and adaptation to experimental shock", Am. J. Physiol. 215:1414-1419.

Audibert et al., 1981, "Active antitoxic immunization by a diphtheria toxin synthetic oligopeptide", Nature 289:593-594.

Beachey, 1985, "Protective immunity evoked by synthetic peptides of Streptoccal M proteins", Adv. Exp. Med. Biol. 185:193-200.

Beidler et al., 1988, Cloning and high level expression of a chimeric antibody with specificity for human carcinoembryonic Antigen, J. Immunol. 141:4053-4060.

Better et al., 1988, "*Escherichia coli* secretion of an active chimeric antibody fragment", Science 240:1041-1043.

Brodeur et al., 1987, "Mouse-human myeloma partners for the production of heterohybridomas", in: *Monoclonal Antibody Production Techniques and Applications*, Marcel Dekker, Inc., New York, pp. 51-63.

Bzik et al., 1986, "The nucleotide sequence of the gB glycoprotein gene of HSV-2 and comparison with the corresponding gene of HSV-1", Virology 155:322-333.

Chang, 2000, "The pharmacological basis of anti-IgE therapy", Nature Biotechnology 18:157-162.

Co et al., 1991, "Humanized antibodies for antiviral therapy", Proc. Natl. Acad. Sci. USA 88:2869.

Cole et al., 1985, "The EBV-hybridoma Technique and its Application to Human Lung Cancer", in: *Monoclonal Antibodies and Cancer Therapy*, Reisfeld and Sell, eds., Alan R. Liss, Inc., NY, pp. 77-96.

Collins et al., 1984, "Nucleotide sequence of the gene encoding the fusion (F) glycoprotein of human respiratory syncytial virus", Proc. Natl. Acad. Sci. USA 81:7683-7687.

Cook et al., 1995, "Photochemically initiated protein splicing", Angew. Chem. Int. Ed. Engl. 34:1629-1630.

Corvalan and Smith, 1987, "Construction and characterisation of a hybrid—hybrid monoclonal antibody recognising both carcinoembryonic antigen (CEA) and vinca alkaloids", Cancer Immunol. Immunother., 24:127-132.

Cruikshank et al., 1997, "A lipidated anti-tat antibody enters living cells and blocks HIV-1 viral replication", J. Acquired Immune Deficiency Syndromes and Human Retrovirology 14:193-203.

Dalrymple et al., 1981, "Antigenic components of Punta Toro virus", in: *The Replication of Negative Strand Viruses*, Bishop and Compans, eds., Elsevier, NY, p. 167-172.

Davis et al., 1991, "Novel structure of the *recA* locus of *Mycobacterium tuberculosis* implies processing of the gene product", J. Bacteriol. 173:5653-5662.

Davis et al., 1992, "Protein splicing in the maturation of *M. tuberculosis* RecA protein: A mechanism for tolerating a novel class of intervening sequence", Cell 71:201-210.

Deguchi et al., 1999, "Retention of biologic activity of human epidermal growth factor following conjugation to a blood-brain drug delivery vector via an extended poly(ethylene glucol) linker", Bioconjugate Chem. 10:32-37.

Den et al., 1999, "A bidirectional phage display vector for the selection and mass transfer of polyclonal antibody libraries", J. Immunol. Meth. 222:45-47.

Emini et al., 1983, "Priming for and induction of anti-poliovirus neutralizing antibodies by synthetic peptides", Nature 304:699.

Ernst et al., 1999, "From IgG monoclonals to IgM-like molecules", Human Antibodies 9:165-170.

Evans and Xu, 1999, "Intein-mediated protein ligation: Harnessing nature's escape artists", Biopolymer 51:333-342.

Evans et al., 1999, "The cyclization and polymerization of bacterially expressed proteins using modified self-splicing inteins", J. Biol. Chem. 274:18359-18363.

Evans et al., 2000, "Protein *trans*-splicing and cyclization by a naturally split intein from the *dnaE* gene of *Synechocystis* species PCC6803", J. Biol. Chem. 275:9091-9094.

Evans et al., 1999, "The *in vitro* ligation of bacterially expressed proteins using an intein from *Methanobacterium thermoautotrophicum*", J. Biol Chem. 274:3923-3926.

Ferguson et al., 1995, "Antigen-based heteropolymers. A potential therapy for binding and clearing autoantibodies via erythrocyte CR1", Arthritis Rheum 38: 190-200.

Foulon et al., 1999, "Preparation and characterization of anti-tenascin monoclonal antibody—streptavidin conjugates for pretargeting applications", Bioconjugate Chem. 10:867-876.

Fuchs et al., 1991, "Targeting recombinant antibodies to the surface of *Escherichia coli*: Fusion to a peptidoglycan associated lipoprotein", Bio/Technology 9:1369-1372.

Ganem and Varmus, 1987, "The molecular biology of the hepatitis B viruses", Ann. Rev. Biochem. 56:651-693.

Garcia et al., 1994, "Evolutionary pattern of human respiratory syncytial virus (subgroup A): Cocirculating lineages and correlation of genetic and antigenic changes in the G glycoprotein", J. Virol 68:5448-5459.

Goding, 1986, "Production of monoclonal antibodies", in: *Monoclonal Antibodies: Principles and Practice*, Academic Press, pp. 59-103.

Gonzales-Scaranto et al., 1982, "Characterization of monoclonal antibodies against the G1 and N proteins of LaCrosse and Tahyna, two California serogroup bunyaviruses", Virology 120:42-53.

Griffiths et al., 1993, "Human anti-self antibodies with high specificity from phage display libraries", EMBO J. 12:725-734.

Haak-Frendscho et al., 1993, "Human IgE receptor α-chain IgG chimera blocks passive cutaneous anaphylaxis reaction in vivo", J. Immunol. 151:351-358.

Hahn et al., 1988, "Nucleotide sequence of Dengue 2 RNA and comparison of the encoded proteins with those of other flaviviruses", Virology 162:167-180.

Hakimi et al., 1990, "The α subunit of the human IgE receptor (FcERI) is sufficient for high affinity IgE binding", J. Biol. Chem. 265:22079-22081.

Hay et al., 1992, "Bacteriophage cloning and *Escherichia coli* expression of a human IgM Fab", Hum. Antibod. Hybridomas 3:81-85.

Ho, 1997, Dynamics of HIV-1 replication in vivo, J. Clin. Invest. 99:2565-2567.

Hogg et al., 1984, "Identification of an anti-monocyte monoclonal antibody that is specific for membrane complement receptor type one ($CR_1$)", Eur. J. Immunol. 14:236-243.

Huse et al., 1989, "Generation of a large combinatorial library of the immunoglobulin repertoire in phage lambda", Science 246:1275-1281.

Jespers et al., 1994, "Guiding the selection of human antibodies from phage display repertoires to a single epitope of an antigen", Bio/technology 12:899-903.

Jones et al., 1986, "Replacing the complementarity-determining regions in a human antibody with those from a mouse", Nature 321:552-525.

Khawli et al., 1993, "Improved immunotargeting of tumors with biotinylated monoclonal antibodies and radiolabeled streptavidin", Antibody Immunoconjugates, Radiopharm. 6:13-27.

Kipriyanov et al., 1996, "Affinity enhancement of a recombinant antibody: formation of complexes with multiple valency by a single-chain Fv fragment-core streptavidin fusion", Protein Engineering 9:203-211.

Kochan et al., 1988, "Isolation of the gene coding for the alpha subunit of the human high affinity IgE receptor", Nucleic Acids Research 16:3584.

Kohler and Milstein, 1975, "Continuous cultures of fused cells secreting antibody of predefined specificity", Nature 256:495-497.

Kozbor et al., 1983, "The production of monoclonal antibodies from human lymphocytes", Immunol. Today 4:72-79.

Kozbor et al., 1984, "A human hybrid myeloma for production of human monoclonal antibodies", J. Immunol., 133:3001-3005.

Lew et al., 1998, "Protein splicing in vitro with a semisynthetic two-component minimal intein", J. Biol. Chem. 273:15887-15890.

Li et al., 1999, "Genetically engineered brain drug delivery vectors: cloning, expression and in vivo application of an anti-transferrin receptor single chain antibody-streptavidin fusion gene and protein", Protein Engineering 12:787-796.

Lindorfer et al., 2001, "Heteropolymer-mediated clearance of immune complexes via erythrocyte CR1: mechanisms and applications", Immunol Rev. 183: 10-24.

Lindorfer et al., 2001, A bispecific dsDNA X monoclonal antibody construct for clearance of anti-dsDNA IgG in systemic lupus erythemotosus, J. Immunol. Meth. 248:125-138.

Liu et al., 1987, "Production of a mouse-human chimeric monoclonal antibody to CD20 with potent Fc-dependent biologic activity", J. Immunol. 139:3521-3526.

Liu et al., 1987, "Chimeric mouse-human IgG1 antibody that can mediate lysis of cancer cells", Proc. Natl. Acad. Sci. USA 84:3439-3443.

Lonberg and Huszar, 1995, "Human antibodies from transgenic mice", Intern. Rev. Immunol. 13:65-93.

Massey and Schochetman, 1981, "Topographical analysis of viral epitopes using monoclonal antibodies: Mechanism of virus neutralization", Virology 115:20-32.

Mathews and Roehrig, 1982, "Determination of the protective epitopes on the glycoproteins of Venezuelan equine encephalomyelitis virus by passive transfer of monoclonal antibodies", J. Immunol. 129:2763-2767.

Matsuno and Inouye, 1983, "Purification of an outer capsid glycoprotein of neonatal calf diarrhea virus and preparation of its antisera", Infection and Immunity 39:155-158.

Mills et al., 1998, "Protein splicing in *trans* by purified N- and C-terminal fragments of the *Mycobacterium tuberculosis* RecA intein", Proc. Natl. Acad. Sci. USA 95:3543-3548.

Milstein, 1990, "Antibodies: a paradigm for the biology of molecular recognition", Proc. R. Soc. London B239:1-16.

Morrison, 1985, "Transfectomas provide novel chimeric antibodies", Science 229:1202-1207.

Morrison et al., 1984, "Chimeric human antibody molecules: Mouse antigen-binding domains with human constant region domains", Proc. Natl. Acad. Sci., 81:6851-6855.

Munson and Robard, 1980, LIGAND: A versatile computerized approach for characterization of ligand-binding systems, Anal. Biochem., 107:220-239.

Nardin et al., 1999, "How are immune complexes bound to the primate erythrocyte complement receptor transferred to acceptor phagocytic cells?", Molec. Immunol. 36:827-835.

Neuberger et al., 1984, "Recombinant antibodies possessing novel effector functions", Nature 312:604-608.

Neurath et al., 1986, "Antibodies to a synthetic peptide from the preS 120-145 region of the hepatitis B virus envelope are virus-neutralizing", Vaccine 4:35-37.

Newton et al., 1983, "Sequence of the hemagglutin gene of influenza virus A/Memphis/1/71 and previously uncharacterized monoclonal antibody-derived variants", Virology 128:495-501.

Nickells et al., 1998, "Mapping epitopes for 20 monoclonal antibodies to CR1", Clin. Exp. Immunol. 112:27-33.

Nishimura et al., 1987, "Recombinant human-mouse chimeric monoclonal antibody specific for common acute lymphocytic leukemia antigen", Canc. Res. 47:999-1005.

Noren et al., 1989, "A general method for site-specific incorporation of unnatural amino acids into proteins", Science 244:182-188.

Noren et al., 2000, "Dissecting the chemistry of protein splicing and its applications", Angew. Chem. Int. Ed. 39:450-466.

O'Shea et al., 1985, "Evidence for distinct intracellular pools of receptors for C3b and C3bi in human neutrophils", J. Immunol. 134:2580-2587.

Oi and Morrison, 1986, "Chimeric antibodies", Bio/Techniques 4:214-221.

Paulus, 1998, "The chemical basis of protein splicing", Chem. Soc. Rev. 27:375-386.

Perler et al., 1997, "Compilation and analysis of intein sequences", Nucleic Acids Res. 25:1087-1093.

Putney et al., 1986, "HTLV-III/LAV-neutralizing antibodies to an *E. coli*-produced fragment of the virus envelope", Science 234:1392-1395.

Queen et al., 1989, "A humanized antibody that binds to the interleukin 2 receptor", Proc. Natl. Acad. Sci. USA 86:10029-10033.

Reichmann et al., 1988, "Reshaping human antibodies for therapy", Nature: 332:323-327.

Rota et al., 1992, "Genetic variability of the glycoprotein genes of current wild-type measles isolates", Virology 188:135-142.

Rothbard and Schoolnik, 1985, "The primary sequence and antigenic structure of gonococcal pilin: approaches towards a gonococcal vaccine", Adv. Exp. Med. Biol. 185:247-273.

Rusckowski et al., 1996, "Imaging osteomyelitis with streptavidin and indium-111-labeled biotin", J. Nucl. Med. 37:1655-1662.

Saban et al., 1994, "Human FcERI-IgG and humanized anti-IgE monoclonal antibody MaE11 block passive sensitization of human and rhesus monkey lung", J. Allergy Clin. Immunol. 94:836-843.

Samuel et al., 1996, "Detection of prosthetic vascular graft infection using avidin/indium-111-biotin scintigraphy", J. Nucl. Med. 37:55-61.

Shaw et al., 1988, "Mouse/human chimeric antibodies to a tumor-associated antigen: Biologic activity of the four human IgG subclasses", J. Natl. Cancer Inst. 80:1553-1559.

Smith et al., 1985, "Measurement of protein using bicinchoninic acid", Anal. Biochem. 150:76-85.

Southworth et al., 1998, :Control of protein splicing by intein fragment reassembly:, EMBO J. 17:918-926.

Steeves et al., 1974, "Structural proteins of mammalian oncogenic RNA viruses; murine leukemia virus neutralization by antisera prepared against purified envelope glycoprotein", J. Virol. 14:187-189.

Subramani et al., 1981, "Expression of the mouse dihydrofolate reductase complementary deoxyribonucleic acid in simian virus 40 vectors", Mol. Cell. Biol. 1:854-864.

Sun et al., 1987, "Chimeric antibody with human constant regions and mouse variable regions directed against carcinoma-associated antigen 17-A", Proc. Natl. Acad. Sci. USA 84:214-218.

Takeda et al., 1985, "Construction of chimaeric processed immunoglobulin genes containing mouse variable and human constant region sequences", Nature, 314, 452-454.

Tempest et al., 1991, "Reshaping a human monoclonal antibody to inhibit human respiratory syncytial virus infection in vivo", Bio-Technology 9:266-271.

Thali et al., 1992, "Cooperativity of neutralizing antibodies directed against the V3 and CD4 binding regions of the human immunodeficiency virus gp120 envelope glycoprotein", J. Acquired Immune Deficiency Syndromes 5:591-599.

Tiollais et al., 1985, "The hepatitis B virus", Nature 317:489-495.

Turner and Kinet, 1999, "Signalling through the high-affinity IgE receptor Fcε RI", Nature 402:B24-B30.

Verhoeyen et al., 1988, "Reshaping human antibodies: Grafting an antilysozyme activity", Science 129:1534-1536.

Wood et al., 1985, "The synthesis and in vivo assembly of functional antibodies in yeast", Nature 314:446-449.

Wu et al., 1998, "Protein *trans*-splicing by a split intein encoded in a split DnaE gene of *Synechocystis* sp. PCC6803", Proc. Natl. Acad. Sci. USA 95:9226-9231.

Zebedee et al., 1992, "Human combinatorial antibody libraries to hepatitis B surface antigen", Proc. Natl. Acad. Sci. USA 89:3175-3179.

McGuinness, Brian T. et al., "Phage diabody repertoires for selection of large numbers of bispecific antibody fragments," *Nature Biotechnology*, vol. 14:1149-1154 (1996).

Plückthun, Andreas et al., "New protein engineering approaches to multivalent and bispecific antibody fragments," *Immunotechnology*, vol. 3:83-105 (1997).

Scott, Charles P. et al., "Production of cyclic peptides and proteins *in vivo*," *PNAS*, vol. 96(24):13638-13643 (1999).

Taylor, Ronald P. et al., "Use of heteropolymeric monoclonal antibodies to attach antigens to the C3b receptor of human erythrocytes: A potential therapeutic treatment," *Proc. Natl. Acad. Sci. USA*, vol. 88:3305-3309 (1991).

European Search Report for Application No. 01988231.5 - 2405, dated Aug. 2, 2004.

International Search Report for Application No. PCT/US01/45653, dated Jun. 21, 2002.

* cited by examiner

C-intein    Pathogen binding moiety

↑ Cys, Ser, or Thr

Transcription or translation →

↓

C-intein

Pathogen binding moiety

FIG. 1b

CLSFGTEILTVEYGPLPIGKIVSEEINCSVYSVDPEGRVYTQAIAQWHDRGEQEVLEYELED
GSVIRATSDHRFLTTDYQLLAIEEIFARQLDLLTLENIKQTEEALDNHRLPFPLLDAGTIK

FIG. 3a

MVKVIGRRSLGVQRIFDIGLPQDHNFLLANGAIAANC

FIG. 3b

FDQMVKFAEY

FIG. 3c

CFNKSHSTAY

METHOD OF PRODUCING BISPECIFIC MOLECULES BY PROTEIN TRANS-SPLICING

This application claims the benefit of U.S. Provisional Patent Application No. 60/244,811, filed on Nov. 1, 2000, which is incorporated herein by reference in its entirety.

1. FIELD OF THE INVENTION

The invention relates to methods of using protein trans-splicing for the production of bispecific molecules having a first antigen recognition portion that binds a C3-like receptor and a second antigen recognition portion that binds a pathogenic antigenic molecule present in the circulatory system of a mammal. The invention also relates to bispecific molecules produced by protein trans-splicing. The invention further relates to methods of using protein trans-splicing for the production of polyclonal libraries of bispecific molecules.

2. BACKGROUND OF THE INVENTION

Primate erythrocytes, or red blood cells (RBC's), play an essential role in the clearance of antigens from the circulatory system. The formation of an immune complex in the circulatory system activates the complement factor C3 in primates and leads to the binding of C3 to the immune complex. The C3/immune complex then binds to the type 1 complement receptor (CR1), a C3 receptor, expressed on the surface of erythrocytes via the C3 molecule attached to the immune complex. The immune complex is then chaperoned by the erythrocyte to the reticuloendothelial system (RES) in the liver and spleen for neutralization. The RES cells, most notably the fixed-tissue macrophages in the liver called Kupffer cells, recognize the C3/immune complex and break this complex from the RBC by severing the C3 receptor-RBC junction, producing a liberated erythrocyte and a C3/immune complex which is then engulfed by the Kupffer cells and is completely destroyed within subcellular organelles of the Kupffer cells. This pathogen clearance process, however, is complement-dependent, i.e., confined to immune complexes recognized by the C3 receptor, and is ineffective in removing immune complexes which are not recognized by the C3 receptor.

Taylor et al. have discovered a complement independent method of removing pathogens from the circulatory system. Taylor et al. have shown that chemical crosslinking of a first monoclonal antibody (mAb) specific to a primate C3 receptor to a second monoclonal antibody specific to a pathogenic antigenic molecule creates a bispecific heteropolymeric antibody which offers a mechanism for binding a pathogenic antigenic molecule to a primate's C3 receptor without complement activation. (U.S. Pat. Nos. 5,487,890; 5,470,570; and 5,879,679). It is found that the Fc portion of the mAb specific to C3 receptor plays an important role in the transfer of the erythrocyte-immune complex to an acceptor cell and the subsequent proteolysis of the erythrocyte-immune complex (Nardin et al., 1999, Molecular Immunology 36:827-835). Taylor et al. have shown that this complement-independent process can remove over 99% of pathogens from the circulation as compared to about 10-15% by the normal, complement-dependent, process.

The Taylor method, however, has certain shortcomings. Firstly, the chemistry of the cross-linking reaction is not very efficient. Typically, the yields of such chemical cross-linking reactions are only about 10% to 20%. As a result, a significant amount of purified mAbs or pathogen-binding moieties is lost during the chemical cross-linking step of the manufacturing process. For example, using standard chemical cross-linking agents (such as Pierce's SATA and sulfo-SMCC), 1 mg of pure mAb1 cross-linked to 1 mg of pure mAb2 will generate only between 0.2 to 0.4 mg of pure product mAb1 X mAb2. Secondly, the bispecific molecule produced by chemical cross-linking contains a chemical cross-linker fragment which can be immunogenic. The immunogenicity of the cross-linker can be disadvantageous when re-administering Taylor's bispecific molecule to the same individual because the individual will generate an immune response against the cross-linker moiety and, upon re-exposure of the same individual to another dose of the bispecific molecule, the individual might mount a vigorous immune response against it, reducing potential therapeutic benefits that the bispecific molecule would otherwise provide. Thirdly, the cross-linking process described in the Taylor patents is not site-specific, and consequently, may decrease somewhat the functionality of the mAbs or pathogen recognition domains. Therefore, there is a need for a more efficient method for the production of bispecific molecules.

Protein splicing is a post-translational protein processing reaction that involves the excision of an intervening sequence, the internal protein domain or intein, from a precursor molecule and the concomitant ligation of the two flanking sequences, the N- and C-terminal external protein domains or N- and C-exteins, to form a functional new protein (see, for example, Paulus, 1998, Chem. Soc. Rev. 27:375-386). The excision and ligation are catalyzed by the amino acid residues within an intein plus the first residue at the N-terminus of the C-extein. The residues responsible for splicing are the approximately 100 amino acids at the intein N-terminus and the approximately 35 amino acids at the intein C-terminus (Lew et al., 1998, J. Biol. Chem. 273:15887-15890; Noren et al., 2000, Angew. Chem. Int. Ed. 39:450-466). A typical protein splicing reaction involves 4 nucleophilic displacements by the 3 conserved splice junction residues: a cysteine (Cys), serine (Ser), or threonine (Thr) at the intein N-terminus, an asparagine (Asn) at the intein C-terminus, and a Cys, Ser, or Thr at the downstream C-extein N-terminus (Perle et al., 1997, Nucleic Acids Res. 25:1087-1093; Southworth et al., 1998, EMBO J. 17:918-926). Other intein residues may also assist in the nucleophilic displacement (Perle et al., 1997, Nucleic Acids Res. 25:1087-1093; Southworth et al. 1998, EMBO J. 17:918-926). Protein splicing has been identified in a variety of species, including eucarya, eubacteria, and archaebacteria.

Inteins may also be split into N-terminal and C-terminal intein fragments that can reconstitute and undergo protein trans-splicing. A naturally occurring split intein system encoded in the DnaE gene of *Synechocystis* sp. PCC6803 (Ssp) was identified (Wu et al., 1998, Proc. Natl. Acad. Sci. USA 95:9226-9231). This split intein system was expressed in *E. coli* and was shown to exhibit trans-splicing activity in *E. coli* cells (Wu et al., 1998, Proc. Natl. Acad. Sci. USA 95:9226-9231). More recently, the Ssp DnaE split intein system has also been shown to mediate efficient in vivo and in vitro trans-splicing and cis-splicing in a foreign extein content (Evans et al., 2000, J. Biol. Chem. 275:9091-9094). Engineered split intein systems based on naturally occurring non-split intein systems have also been demonstrated, including the in vitro trans-splicing systems using purified N- and C-terminal fragments of the *Mycobacterium tuberculosis* (Mtu) RecA intein and the *Pyrococcus* sp. (Psp) Pol-1 intein (Mills et al., 1998, Proc. Natl. Acad. Sci. USA 95:3543-3548; Lew et al., 1998, J. Biol. Chem. 273:15887-15890; Southworth et al., 1998, EMBO J. 17:918-926). It is shown that the N- and C-terminal fragments of the Mtu RecA intein system can be reconstituted as an inactive disulfide-linked complex of the two intein fragments, which can subsequently undergo trans-splicing reaction by reduction of the disulfide bond.

Inteins and split inteins may also be modified for more efficient and/or controllable splicing and trans-splicing reactions. For example, splicing in chimeric precursors is usually less efficient than in native precursors, presumably due to impaired intein folding in a foreign extein content as evidenced by their temperature-dependent reactivity. (Noren et al., 2000, Angew. Chem. Int. Ed. 39:450-466) Evans et al. show that inclusion of 3 to 5 native extein residues in the N- and C-inteins of Ssp DnaE system may enhance trans-splicing and cis-splicing in a foreign extein content (Evans et al., 2000, J. Biol. Chem. 275:9091-9094). Alternatively, it may be desirable to choose exteins comprising proximal amino acid sequences that are similar to the native exteins. The inteins themselves may also be modified. For example, it is shown that splicing proficiency in E coli is increased when the proline residue adjacent to the N-terminal Cys in the ribonucleoside diphosphate reductase gene of Methanobacterium thermoautotrophicum is replaced with an alanine residue (Evans et al., 1999, J. Biol. Chem. 274:3923-3926). Inteins have also been modified by site-directed mutagenesis so that splicing reactions can be controlled by photochemistry (Cook et al., 1995, Angew. Chem. 107:1736-1737; Cook et al., 1995, Angew. Chem. Int. Ed. Engl. 34:1629-1630; Noren et al., 1989, Science 244:182-188).

Means for fusing proteins and/or synthetic polypeptides based on protein splicing and trans-splicing have been reported (see, for example, Evans et al., 1999, Biopolymer 51:333-341; Evans et al., 1999, J. Biol. Chem. 274:3923-3926; Evans et al., 1999, J. Biol. Chem. 274:18359-18363). In vitro trans-splicing generally offers a more controlled means in utilizing protein splicing in protein synthesis. Reconstitution and trans-splicing in vitro also allows ligation of exteins expressed in different cells. This has also allowed expression of proteins that are otherwise not possible in a single cell (Noren et al., 2000, Angew. Chem. Int. Ed. 39:450-466). On the other hand, in vivo trans-splicing may be more efficient in that the co-expressed inteins may be less prone to misfolding, due both to more efficient reconstitution and/or the assistance of the powerful protein folding machinery present in a cell (Southworth et al., 1998, EMBO J. 17:918-926).

Discussion or citation of a reference herein shall not be construed as an admission that such reference is prior art to the present invention.

3. SUMMARY OF THE INVENTION

The present invention relates to methods of producing a bispecific molecule having a first antigen recognition portion that binds a C3-like receptor and a second antigen recognition portion that binds a pathogenic antigenic molecule, using protein trans-splicing. In the present invention, the first antigen recognition portion is conjugated to the N-terminus of an N-intein of a suitable split intein to produce an N-intein first antigen recognition portion fragment, whereas the second antigen recognition portion is conjugated to the C-terminus of the C-intein of the split intein to produce a C-intein second antigen recognition portion fragment. The N-intein first antigen recognition portion fragment and the C-intein second antigen recognition portion fragment are then brought together such that they reconstitute and undergo trans-splicing to produce the bispecific molecule. The bispecific molecule of the present invention is useful in the clearance of pathogenic antigenic molecule from the circulatory system of a mammal.

The first antigen recognition portion of the present invention can be any molecule or fragment thereof having a C3-like receptor binding domain and an effector domain. In a preferred embodiment, the first antigen recognition portion comprises an anti-CR1 monoclonal antibody. The first antigen recognition portion can also be a single chain Fv fragment fused to an Fc domain or a chimeric antibody having a C3-like receptor binding domain and an effector domain.

The second antigen recognition portion of the present invention can be any molecule or fragment thereof that recognizes and binds a pathogenic antigenic molecule, e.g., a naturally occurring antigen, and/or any derivative or fragment thereof. The pathogenic antigenic molecule can be any substance that is present in the circulation that is potentially injurious to or undesirable in the subject to be treated, including but is not limited to proteins or drugs or toxins, autoantibodies or autoantigens, or a molecule of any infectious agent or its products. A pathogenic antigenic molecule is any molecule containing an antigenic determinant (or otherwise capable of being bound by a binding domain) that is or is part of a substance (e.g., a pathogen) that is the cause of a disease or disorder or any other undesirable condition. The second antigen recognition portion of the invention can be any type of molecule, including but is not limited to peptide and polypeptide, nucleic acid, oligosaccharide, and organic small molecule.

The first and second antigen recognition portions of the bispecific molecule of the invention can be linked directly. The first and second antigen recognition portions of the bispecific molecule of the invention can also be linked via a suitable linker, such as but is not limited to a peptide linker, a Poly(ethylene glycol) (PEG) linker, a streptavidin-biotin or avidin-biotin linker, or a combination thereof. In preferred embodiments of the invention, the first and second antigen recognition portions are conjugated by site-specific linkage. The linkage can be covalent bond(s) and/or non-covalent bonds, such as but is not limited to hydrogen bond(s).

The bispecific molecule of the invention can contain a single second antigen recognition portion conjugated to the first antigen recognition portion. Alternatively, the bispecific molecule of the invention can also contain two or more second antigen recognition portions conjugated to different regions of the first antigen recognition portion. For example, the bispecific molecule can contain two second antigen recognition portions conjugated to each of the heavy chains of a first antigen recognition monoclonal antibody. When two or more second antigen recognition portions are contained in the bispecific molecule, such second antigen recognition portions can be the same or different antigen recognition portions. The first and second second antigen recognition portions can be different antigen recognition portions that target the same antigen to be cleared. In a preferred embodiment of the invention, the first and second second antigen recognition portions target an antigenic molecule to be cleared cooperatively. As a non-limiting example, one of the second antigen recognition portions may enhance the binding of the other second antigen recognition portion to a pathogenic antigenic molecule, thereby facilitating the removal of the pathogenic antigenic molecule. The first and second second antigen recognition portions can also be different antigen recognition portions that target different pathogenic antigenic molecules to be cleared.

The present invention makes use of various split inteins for the production of bispecific molecules. In one aspect of the invention, naturally occurring split inteins are used for the production of bispecific molecules. In another aspect of the invention, engineered split intein based on naturally occurring non-split inteins are used for the production of bispecific molecules. In various embodiments of the invention, a split intein can be modified by adding, deleting, and/or mutating one or more amino acid residues to the N-intein and/or the C-intein such that the modification improves or enhances the intein's proficiency in trans-splicing and/or permits control of trans-splicing processes. In one preferred embodiment, a Cys residue can be included at the carboxy terminus of a C-intein so that the requirement that the molecular moiety conjugated to the C-intein must start with a Cys is alleviated. In other preferred embodiments, one or more native proximal extein residues are added to the N- and/or C-intein to facilitate trans-splicing in a foreign extein content.

In a preferred embodiment of the invention, the trans-splicing system of the split intein encoded in the DnaE gene of *Synechocystis* sp. PCC6803 is used. In another embodiment of the invention, an engineered split intein system based on the *Mycobacterium tuberculosis* RecA intein is used. The production of bispecific molecules can be carried out in vitro wherein the intein antigen recognition portion fragments are expressed in separate hosts. The production of bispecific molecules can also be carried out in vivo. In one embodiment, nucleic acids encoding the intein antigen recognition portion fragments are inserted into separate vectors which are then co-transfected into a host for in vivo production of the bispecific molecule. In another embodiment, nucleic acids encoding the intein fragments are inserted into the same vector which is then transfected into a host for in vivo production of the bispecific molecule.

In the present invention, the N-intein first antigen recognition portion fragment is preferably produced by fusing an appropriate antigen recognition moiety that binds a C3-like receptor to the N-terminus of the N-intein of a suitable split intein. In a preferred embodiment, the C-terminus of the heavy chain of an anti-CR1 mAb is fused to the N-terminus of the N-intein of a split intein.

In the present invention, the C-intein second antigen recognition portion fragment is preferably produced by fusing an appropriate antigen recognition moiety that binds an pathogenic antigenic molecule to be cleared to the C-terminus of the C-intein of a suitable split intein. The amino acid residue immediately at the C-terminal side of the splice junction of the C-intein is a cysteine, serine, or threonine. In another embodiment of the invention, a C-intein streptavidin is produced by fusing a streptavidin to the C-terminus of a C-intein comprising a Cys, Ser, or Thr immediately downstream of the splice junction and is used in trans-splicing to produce a first antigen recognition portion-streptavidin fusion molecule which subsequently reacts with a biotinylated second antigen recognition portion to produce the bispecific molecule. It is also understood that other molecules that specifically bind biotin, including but not limited to avidin, are also within the scope of the present invention.

In one embodiment of the present invention, the bispecific molecule is produced by mixing the N-intein first antigen recognition portion fragment and the C-intein second antigen recognition portion fragment in vitro so that the fragments reconstitute and undergo trans-splicing. In another embodiment of the invention, a first antigen recognition portion-streptavidin molecule is produced by mixing the N-intein first antigen recognition portion fragment and the C-intein streptavidin fragment in vitro to produce a first antigen recognition portion-streptavidin molecule. The bispecific molecule is then produced by reaction of the first antigen recognition-streptavidin molecule with a biotinylated second antigen recognition portion. It is also understood that other molecules that specifically bind biotin, such as but is not limited to avidin, are also within the scope of the present invention.

The present invention also relates to the production of polyclonal libraries of bispecific molecules. In one embodiment of the invention, a library of bispecific molecules that target multiple epitopes of a pathogenic antigenic molecule is produced using trans-splicing for conjugating each member of a population of second antigen recognition portions, such as those selected from a sufficiently large phage display library, to an anti-CR1 monoclonal antibody (mAb). In a preferred embodiment, the polyclonal library is produced without clonal separation of individual members from the population of selected second antigen recognition portions. Polyclonal libraries of bispecific molecules that target multiple variants of a pathogenic antigenic molecule are also envisioned. In another embodiment of the invention, the polyclonal library of bispecific molecules is produced using the streptavidin-biotin configuration of the present invention. In still another embodiment of the invention, a plurality of N-intein anti-CR1 mAb fragments comprising a plurality of different anti-CR1 mabs that target different sites on the red blood cells are mixed with the plurality of C-intein antigen recognition portion fragments with a plurality of specificities to produce a polyclonal library of bispecific molecules having polyclonal first and second antigen recognition portions.

The present invention also provides nucleic acids encoding the bispecific molecules of the invention as well as intermediate molecules of the invention.

The present invention also provides cells that contain the bispecific molecules and cells that are transformed by vectors encoding intermediate molecules.

The present invention also provides kits containing the intein antigen recognition portion fragments of the invention, or one or more nucleic acids encoding the intein antigen recognition portion fragments of the invention, or cells transformed with such nucleic acids, in one or more containers. Such kits can be used to practice the present invention.

The present invention further provides methods for using the bispecific molecules in the treatment of various disorders.

4. BRIEF DESCRIPTION OF FIGURES

FIGS. 1*a*-1*e* illustrate some preferred embodiments of the bispecific molecules of the present invention. FIG. 1*a*: schematic illustration of N-intein anti-CR1 fragment; FIG. 1*b*: schematic illustration of C-intein pathogen binding moiety fragment; FIG. 1*c*: schematic illustration of C-intein streptavidin fragment; FIG. 1*d*: schematic illustration of some configurations of bispecific molecules; FIG. 1*e*: schematic illustration of some configurations of bispecific molecules including a streptavidin-biotin linker.

FIG. 2 illustrates process of producing bispecific molecules using protein trans-splicing.

FIGS. 3*a*-3*d* illustrate the amino acid sequence of the naturally occurring split intein encoded in the DnaE gene of Ssp (Wu et al., 1998, Proc. Natl. Acad. Sci. USA 95:9226-9231). FIG. 3*a*: amino acid sequence of the N-intein (SEQ ID NO:1); FIG. 3*b*: amino acid sequence of the C-intein, including the immediate downstream cysteine (SEQ ID NO:2); FIG. 3*c*: amino acid sequence of the first ten N-extein residues (SEQ ID NO:3); FIG. 3*d*: amino acid sequence of the first ten C-extein residues (SEQ ID NO:4).

5. DETAILED DESCRIPTION OF THE INVENTION

The present invention provides methods utilizing protein trans-splicing for producing bispecific molecules that bind both a C3-like receptor, or its functional equivalent, and an antigenic molecule to be cleared from the circulation.

The N- and C-intein from a split intein system are linked to a C3-like receptor recognition portion and an antigen recognition portion respectively. Subsequent reconstitution and trans-splicing reactions ligate the two antigen recognition portions and produce a bispecific molecule. The method for producing bispecific molecules using protein trans-splicing is site-specific, permitting the design and construction of bispecific molecules with particular structure and function(s). The invention also relates to methods of utilizing protein trans-splicing to ligate a C3-like receptor recognition portion with an antigen recognition portion through a streptavidin-biotin or avidin-biotin linker. Although hereinafter, streptavidin is referred, it is understood that avidin can be used to in place of streptavidin and therefore is within the scope of the present invention. In this configuration of the invention, rather than being directly linked to an antigen recognition portion, the C-intein is linked to a streptavidin. Streptavidin has been given to humans without eliciting an immunological response (Li et al., 1999, Protein Engineering 12:787-796; Rusckowski et al., 1996, J. Nucl. Med. 37:1655-1662; Samuel et al., 1996, J. Nucl. Med. 37:55-61). Reconstitution and trans-splicing produce a molecule consisting of a C3-like receptor recognition portion ligated to a streptavidin. This molecule can then be conjugated with an antigen recognition portion by reacting with a biotinylated antigen recognition portion. This configuration of the invention is particularly useful in producing bispecific molecules that comprises a monoclonal antibody (mAb) as the antigen recognition portion. This configuration of the invention is also particularly useful in producing bispecific molecules wherein the antigen recognition portion is a non-proteinaceous moiety, such as a nucleic acid or an organic small molecule. The invention further relates to methods of producing polyclonal libraries of bispecific molecules using protein trans-splicing.

A bispecific molecule generally refers to a molecule having two or more different antigen recognition specificities. The bispecific molecule of the present invention refers to a molecule having a first antigen recognition portion that binds a C3-like receptor, such as the type 1 complement receptor in primates, and a second antigen recognition portion that binds a pathogenic antigenic molecule. The pathogenic antigenic molecule is desired to be cleared from the circulation. The first and second antigen recognition portions are linked by sufficiently strong linkage such that the first and second antigen recognition portions form a stable association, preferably the linkage is site-specific to one or both antigen recognition portions. In a preferred configuration, the first and second antigen recognition portions are linked by a peptide bond. The first and second antigen recognition portions can also be linked through a spacer or linker, such as but is not limited to a peptide linker, a Poly(ethylene glycol) (PEG) linker, or a streptavidin-biotin linker.

As used herein, the term "antigen recognition portion" refers to a molecular moiety that recognizes and binds an antigenic molecule or, alternatively, is recognized and bound by an antigenic molecule. The molecular moiety can contain antigen binding domain(s) and effector domain(s). An effector domain refers to a portion of the molecular moiety that facilitates the transfer of the blood cell-immune complex, such as the erythrocyte-immune complex in primate, to an acceptor cell for proteolysis. For example, an effector domain can comprise an Fc domain of an mAb, i.e., a hinge region, a CH2 domain and a CH3 domain of a heavy chain. Alternatively, an effector domain can comprise an Fc domain with the CH2 domain and the CH3 domain in reverse order, i.e., the CH3 domain appears at the amino terminal side of the CH2 domain.

As used herein, the term "molecular moiety" encompasses any molecule or fragment thereof, including but are not limited to peptides and polypeptides, nucleic acids, oligosaccharide, organic small molecules, and any combination thereof.

As used herein, the term "site-specific linkage" encompasses any linkage that connects two molecular moieties at defined site(s). The linkage can be formed by a covalent bond, such as but is not limited to a covalent peptide bond.

The linkage can also be formed by other type of bond(s), such as but are not limited to hydrogen bond(s).

As used herein, the term "C3-like receptor" refers to any mammalian circulatory molecule expressed on the surface of a mammalian blood cell, which has an analogous function to a primate C3 receptor, the CR1, in that it binds to a molecule associated with an immune complex, which is then chaperoned by the blood cell to a phagocytic cell for clearance. A mammalian blood cell can be, but is not limited to, a primate red-blood cell or erythrocyte.

As used herein, the term "protein trans-splicing" refers to protein splicing reactions that involve split intein systems. A split intein system refers to any intein system wherein a peptide bond break exists between the amino terminal and carboxy terminal amino acid sequences such that the N-terminal and C-terminal sequences become separate molecules which can reassociate, or reconstitute, into a functional trans-splicing element. The split intein system can be a naturally occurring split intein system, which encompasses any split intein systems that exist in natural organisms. The split intein system can also be an engineered split intein system, which encompasses any split intein systems that are generated by separating a non-split intein into an N-intein and a C-intein by any standard methods known in the art. As a non-limiting example, an engineered split intein system can be generated by breaking a naturally occurring non-split intein into appropriate N- and C-terminal sequences. Preferably, such engineered intein systems comprise only the amino acid sequences essential for trans-splicing reactions.

As used herein, the term "N-terminal intein" or "N-intein" refers to any intein sequence that comprises the essential N-terminal amino acid sequences and that is functional for trans-splicing reactions. An "N-intein" thus also comprises a sequence that is spliced out when transplicing occurs. An N-intein can comprise a sequence that is a modification of a naturally occurring N-intein sequence. For example, an N-intein can comprise additional amino acid residues and/or mutated residues so long as the inclusion of such additional and/or mutated residues does not render the N-intein non-functional in trans-splicing. Preferably, the inclusion of the additional and/or mutated residues improves or enhances the N-intein's proficiency in trans-splicing and/or permits control of trans-splicing processes. In some embodiments of the invention, an "N-intein moiety" is used to refer to a molecule that comprises an N-intein and optionally a linker sequence; this linker sequence can be but is not limited to a peptide linker, a streptavidin-biotin linker, or a PEG linker, at the N-terminus of the N-intein. The terminus of an N-intein moiety is referred as the "N-terminal end" of the N-intein moiety, to which another molecule can be conjugated. When the linker is a peptide linker, the N-intein moiety is also referred to herein as an "N-intein peptide" and the "N-terminal end" is the N-terminus of the N-intein peptide.

As used herein, the term "C-terminal intein" or "C-intein" refers to any intein sequence that comprises the essential C-terminal amino acid sequences and that is functional for trans-splicing reactions. A "C-intein" thus also comprises a sequence that is spliced out when transplicing occurs. A C-intein can comprise a sequence that is a modification of a naturally occurring C-intein sequence. For example, a C-intein can comprise additional amino acid residues and/or mutated residues so long as the inclusion of such additional and/or mutated residues does not render the C-intein nonfunctional in trans-splicing. Preferably, the inclusion of the additional and/or mutated residues improves or enhances the C-intein's proficiency in trans-splicing and/or permits control of trans-splicing processes. As a non-limiting example, a Cys residue can be included at the carboxy terminus of a C-intein so that the requirement that the molecular moiety conjugated to the C-intein must start with a Cys is alleviated. In some embodiments of the invention, a "C-intein moiety" is used to refer to a molecule that comprises a C-intein and optionally a linker sequence; this linker can be but is not limited to a peptide linker, a streptavidin-biotin linker, or a PEG linker, at the C-terminus of the C-intein. The terminus of a C-intein moiety is referred as the "C-terminal end" of the C-intein moiety, to which another molecule can be conjugated. When the linker is a peptide linker, the C-intein moiety is also referred to herein as a "C-intein peptide" and the "C-terminal end" is the C-terminus of the C-intein peptide.

As used herein, the term "N-terminal extein" or "N-extein" refers to any molecular moiety conjugated to the amino terminus of an N-intein.

As used herein, the term "C-terminal extein" or "C-extein" refers to any molecular moiety conjugated to the carboxy terminus of a C-intein.

As used herein, a polyclonal library of bispecific molecules of the present invention refers to a plurality of bispecific molecules each having a first antigen recognition portion that binds a C3-like receptor and a second antigen recognition portion that binds an antigen to be cleared, the library comprising a plurality of second antigen recognition portions with a plurality of different specificities. Preferably, the plurality of bispecific molecules of the polyclonal library includes specificities for different epitopes of an antigenic molecule and/or for different variants of an antigenic molecule. More preferably, the plurality of bispecific molecules of the polyclonal population includes specificities for a substantial portion of naturally-occurring variants of an antigenic molecule. The polyclonal library can also include specificities for a mixture of different antigenic molecules. In preferred embodiments, at least 90%, 75%, 50%, 20%, 10%, 5%, or 1% of bispecific molecules in the polyclonal population target the desired antigenic molecule and/or antigenic molecules. In other preferred embodiments, the proportion of any single bispecific molecule in the polyclonal population does not exceed 90%, 50%, or 10% of the population. The polyclonal library comprises at least 2 different bispecific molecules with different specificities. More preferably, the polyclonal library comprises at least 10 different bispecific molecules with different specificities. Most preferably, the polyclonal library comprises at least 100 different bispecific molecules with different specificities.

As used herein, a cocktail of bispecific molecules of the present invention refers to a mixture of purified bispecific molecules blended together for targeting one or a mixture of antigens. In particular, the cocktail of bispecific molecules refers to a mixture of purified bispecific molecules having a plurality of second antigen recognition portions that target different or same antigenic molecules and that are of mixed types. For example, the mixture of the second antigen recognition portions can be a mixture of peptides, nucleic acids, and/or organic small molecules. A cocktail of bispecific molecules can generally be prepared by mixing various purified bispecific molecules.

Section 5.1. below describes the bispecific molecules of the present invention. Section 5.2. describes protein trans-splicing systems that can be used in the present invention. Split inteins and methods for their production are described in the section. Section 5.3. describes the production and purification of bispecific molecules using protein trans-splicing. Procedures for the preparation of intein fragments, methods for the production of bispecific molecules using such intein fragments in vitro and in vivo, and methods for the purification and characterization of bispecific molecules are described in this section in detail. Section 5.4. describes the production of polyclonal libraries of bispecific molecules using protein trans-splicing. Section 5.5. describes methods of using the bispecific molecules of the invention in the treatment of various diseases. Section 5.6. describes kits of materials that can be used to practice the invention. Section 5.7. describes applications of the methods of the present invention in the production of other bispecific molecules.

5.1. Bispecific Molecules

In the present invention, the first antigen recognition portion of the bispecific molecule can be any polypeptide that contains a CR1 binding domain and an effector domain. In a preferred embodiment, the first antigen recognition portion is an anti-CR1 mAb. In another embodiment, the first antigen recognition portion is an anti-CR1 polypeptide antibody, including but is not limited to, a single-chain variable region fragment (scFv) with specificity for a C3-like receptor fused to the N-terminus of an immunoglobulin Fc domain. The first antigen binding portion can also be a chimeric antibody, such as but is not limited to a humanized monoclonal antibody wherein the complementarity determining regions are mouse, and the framework regions are human thereby decreasing the likelihood of an immune response in human patients treated with the antibody (U.S. Pat. Nos. 4,816,567, 4,816,397, 5,693,762; 5,585,089; 5,565,332 and 5,821,337 which are incorporated herein by reference in their entirety). Preferably, the Fc domain of the chimeric antibody can be recognized by the Fc receptors on phagocytic cells, thereby facilitating the transfer and subsequent proteolysis of the RBC-immune complex. Although, for simplicity, this disclosure often makes references to an anti-CR1 antigen recognition portion or an anti-CR1 antibody, it is understood that such antigen recognition portion or antibody refers to an antigen recognition portion or antibody that binds any C3-like receptor.

In the present invention, the second antigen recognition portion of the bispecific molecule can be any molecular moiety, including but are not limited to any antibody or antigen binding fragments thereof, that recognizes and binds a pathogenic antigenic molecule. For example, the second antigen recognition portion can be an epitope or antigenic determinant that is bound by an antibody to be cleared from the circulatory system, such as that responsible for an autoimmune disease.

As used herein, "epitope" refers to an antigenic determinant, i.e., a region of a molecule that provokes an immunological response in a host or is bound by an antibody. This region can but need not comprise consecutive amino acids. The term epitope is also known in the art as "antigenic determinant." An epitope may comprise as few as three amino acids in a spatial conformation which is unique to the immune system of the host. Generally, an epitope consists of at least five such amino acids, and more usually consists of at least 8-10 such amino acids. Methods for determining the spatial conformation of such amino acids are known in the art.

The second antigen recognition portion of the bispecific molecule can also be a non-proteinaceous moiety. In one embodiment, the second antigen recognition portion is a nucleic acid. In another embodiment, the second antigen recognition portion is an organic small molecule. In still another embodiment, the second antigen binding portion is an oligosaccharide.

In preferred embodiments of the invention, the bispecific molecule comprises an anti-CR1 mAb and two second antigen recognition portions: a first, second antigen recognition portion fused to the C-terminus of a first heavy chain of the anti-CR1 mAb and a second, second antigen recognition portion fused to the C-terminus of a second heavy chain of the anti-CR1 mAb. In some embodiments, the two second antigen recognition portions are the same antigen recognition portions. In other embodiments, the two second antigen recognition portions are different antigen recognition portions. The two second antigen recognition portions can be different antigen recognition portions that target the same antigenic molecule to be cleared. In a preferred embodiment of the invention, the two second antigen recognition portions target an antigenic molecule to be cleared cooperatively. As a non-limiting example, one of the second antigen recognition portions induces conformation alterations of the antigenic molecule so as to enhance the binding affinity of the other second antigen recognition portion, thereby facilitating the removal of the antigenic molecule (Thali et al., J. Acquired Immune Deficiency Syndromes 5:591-599). The two second antigen recognition portions can also be different antigen recognition portions that target different antigens to be cleared. The second antigen recognition portion can be, but is not limited to, an antigen binding domain, an epitope, a nucleic acid, or an organic small molecule.

In other preferred embodiments of the invention, the bispecific molecule comprises an anti-CR1 mAb and two second antigen recognition portions: a first, second antigen recognition portion fused to the C-terminus of a first light chain of the anti-CR1 mAb and a second, second antigen recognition portion fused to the C-terminus of a second light chain of the anti-CR1 mAb. In some embodiments, the two second antigen recognition portions are the same antigen recognition portions. In other embodiments, the two second antigen recognition portions are different antigen recognition portions. The two second antigen recognition portions can be different antigen recognition portions that target the same antigenic molecule to be cleared. In a preferred embodiment of the invention, the two second antigen recognition portions target an antigenic molecule to be cleared cooperatively. As a non-limiting example, one of the second antigen recognition portions may induce conformation alterations of the antigenic molecule so as to enhance the binding of the other second antigen recognition portion, thereby facilitating the removal of the antigenic molecule (Thali et al., J. Acquired Immune Deficiency Syndromes 5:591-599). The two second antigen recognition portions can also be different antigen recognition portions that target different antigens to be cleared. The second antigen recognition portion can be, but is not limited to, an antigen binding domain, an epitope, a nucleic acid, or an organic small molecule.

Although in preferred embodiments of the invention, the second antigen recognition portion(s) is conjugated to either the heavy or the light chains of an anti-CR1 mAb, it is understood that other configurations are also encompassed by the invention. Non-limiting examples include but are not limited to configurations in which one second antigen recognition portion conjugates to a heavy chain and another second antigen recognition portion conjugates to a light chain. Configurations comprising more than two second antigen recognition portions conjugated to one anti-CR1 mAb are also envisioned.

In another embodiment of the invention, the bispecific molecule comprises an anti-CR1 mAb and an antigen recognition portion fused to the C-terminus of one of the heavy chains of the anti-CR1 mAb. In still another embodiment of the invention, the bispecific molecule comprises an anti-CR1 mAb and an antigen recognition domain fused to the C-terminus of one of the light chains of the anti-CR1 mAb. In still another embodiment of the invention, the bispecific molecule comprises an anti-CR1 polypeptide antibody, including but is not limited to, a scFv with specificity for a C3-like receptor fused to the N-terminus of an immunoglobulin Fc domain, and an antigen recognition domain fused to the C-terminus of the anti-CR1 polypeptide. The antigen recognition domain can be, but is not limited to, an antigen binding domain, an epitope, a nucleic acid, or an organic small molecule.

It is understood that, in any embodiments described supra, the first and second antigen recognition portions can also be linked via a linker. In a preferred embodiment of the invention, the first and second antigen recognition portions are linked by a peptide linker. In other preferred embodiments, the first and second antigen recognition portions are linked via a streptavidin-biotin or a PEG linker.

5.2. Protein Trans-splicing System

The present invention contemplates a method of utilizing protein trans-splicing for the production of bispecific molecules. The method can be used to directly or via a linker conjugate a first antigen recognition portion, including but is not limited to an anti-CR1 mAb, with a second antigen recognition portion, including but is not limited to a peptide or polypeptide, a nucleic acid, and an organic small molecule, to form a bispecific molecule. Alternatively, the method can be used to conjugate a first antigen recognition portion with streptavidin to form a first antigen recognition portion-streptavidin fusion molecule which can be conjugated with a biotinylated second antigen recognition portion.

In the present invention, the N-terminus of an N-intein of a split intein is fused to a C-terminus of a C3-like receptor recognition portion, such as but is not limited to an anti-CR1 mAb, whereas the C-terminus of a corresponding C-intein is conjugated with an antigen recognition portion. Any proteinaceous and non-proteinaceous antigen recognition moieties can be conjugated to the C-intein either directly or via a linker, such as but is not limited to a peptide linker, a streptavidin-biotin linker, or a PEG linker. The N-intein anti-CR1 mAb and the C-intein antigen recognition portion can then undergo reconstitution and trans-splicing whereby the C3-like receptor recognition portion and the antigen recognition portion are ligated to form a bispecific molecule. Any split intein systems, including but is not limited to the naturally occurring split intein system based on the DnaE gene of *Synechocystis* sp. PCC6803, can be used in the present invention. Naturally occurring non-split intein systems, such as but is not limited to the *Mycobacterium tuberculosis* RecA intein may also be used. When such intein systems that are not split intein systems in their native state are to be used, engineered split inteins can be obtained by separating a non-split intein into an N-intein and a C-intein by any standard molecular biological methods known in the art. Preferably, such engineered split inteins are constructed such that each of the N- and C-inteins comprises only the amino acid sequence essential for trans-splicing reaction. For example, any homing endonuclease sequence within a naturally occurring non-split intein can be removed without affecting the capability of the resultant split intein for trans-splicing reaction. The sequences that are to be included in an engineered split intein will be apparent to one skilled in the art.

5.2.1. Trans-splicing System Based on Naturally Occurring Split Inteins

In one embodiment of the present invention, naturally occurring split inteins are used in the production of bispecific molecules of the invention. In a preferred embodiment, the trans-splicing system of the split intein encoded in the DnaE gene of *Synechocystis* sp. PCC6803 is used. The Ssp DnaE intein comprises a 123-amino acid N-terminal intein sequence (the Ssp 123 aa N-intein) and a 36-amino acid C-terminal intein sequence (the Ssp 36 aa C-intein). The nucleic acid sequences encoding the Ssp 123 aa N-intein and the Ssp 36 aa C-intein are displayed in FIG. 3.

In one embodiment, the Ssp 123 aa N-intein is used to prepare the N-intein first antigen recognition portion fragment, i.e., the N-intein anti-CR1. The N-terminus of the Ssp 123 aa N-intein is fused to the C-terminus of a C3-like receptor recognition portion, such as but is not limited to an anti-CR1 mAb.

In another embodiment, the Ssp 36 aa C-intein is used to prepared the C-intein second antigen recognition portion fragment. The C-terminus of the Ssp 36 aa C-intein is conjugated with an antigen recognition portion having a Cys, Ser, or Thr at its N-terminus.

In another embodiment of the present invention, a 37 aa C-intein which adds a Cys, Ser, or Thr residue to the C-terminus of the Ssp 36 aa C-intein is used to prepare the C-intein second antigen recognition portion fragment. This 37 aa C-intein can be conjugated with any antigen recognition moiety, both proteinaceous and non-proteinaceous.

In still another embodiment of the present invention, one or more native proximal N-extein residues are added to the N-terminus of the Ssp 123 aa N-intein to form an N-intein of the invention. As used herein, "native proximal N-extein residues" refers to amino acid residues immediately upstream, i.e., at the amino terminal side, to the splice junction and having sequence identical to that in the native N-extein. In a preferred embodiment, 2 or more native proximal N-extein residues are added to the Ssp 123 aa N-intein. Such N-intein is then used to prepare the N-intein first antigen recognition portion fragment.

In still another embodiment of the present invention, one or more native proximal C-extein residues are added to the C-terminus of the Ssp 36 aa C-intein to form a C-intein of the invention. As used herein, "native proximal C-extein residues" refers to amino acid residues immediately downstream, i.e., at the carboxy terminal side, to the splice junction having sequence identical to that in the native C-extein. In a preferred embodiment, 3 or more native proximal C-extein residues are added to the Ssp 36 aa C-intein. Such C-intein is then used to prepare C-intein antigen recognition portion fragment.

In another embodiment, unnatural amino acid residues, such as but is not limited to an amino acid residue containing a caged photoreactive group, such as O-(2-nitrobenzyl) serine, can be incorporated at the N-terminus of an N-intein by site-directed mutagenesis so that splicing reactions can be activated by irradiation of light of an appropriate wavelength, preferably a wavelength in the range of 300-350 nm. Other intein systems that permit controllable trans-splicing can also be designed by known methods in the art and are considered to be within the scope of the invention.

Nucleic acids encoding the Ssp 123 aa N-intein and any of the modified Ssp N-inteins can be produced by standard methods known in the art. In one embodiment, the nucleic acids encoding an Ssp N-intein is synthesized by annealing a set of oligonucleotides comprising nucleotide sequences that span the nucleotide sequence of the desired N-intein. In another embodiment, the nucleic acids encoding an N-intein can be produced by amplification from an appropriate plasmid, such as but is not limited to the plasmid pDnaE-C-209, with appropriate primers, see Evans et al., 2000, J. Biol. Chem. 275:9091-9094. The nucleic acids encoding an N-intein can then be used in the construction of expression vectors.

Nucleic acids encoding the Ssp 36 aa C-intein and any of the modified Ssp C-intein can be produced by standard methods known in the art. In one embodiment, the nucleic acids encoding an Ssp C-intein is synthesized by annealing a set of oligonucleotides comprising nucleotide sequences that span the nucleotide sequence of the desired C-intein. In another embodiment, the nucleic acids encoding an C-intein can be produced by amplification from an appropriate plasmid by any standard method known in the art. The nucleic acids encoding a C-intein can then be used in the construction of expression vectors.

Alternatively, the Ssp N-inteins and C-inteins can be produced by peptide synthesis techniques. Any peptide synthesis techniques can be used for this purpose. It will be recognized by one skilled in the art that a multi-step peptide synthesis can be used for the synthesis of N-inteins. The synthesized N- and C-intein can then be chemically conjugated with antigen recognition portions by any methods known in the art.

5.2.2. Trans-splicing System Based on Engineered Split Inteins

In another embodiment of the present invention, the trans-splicing system of engineered split inteins are used in the production of bispecific molecules of the invention. Examples of engineered split intein systems include but is not limited to that based on the Mtu RecA intein. An engineered Mtu RecA intein can comprise an N-terminal intein sequence of 105 amino acids (Mtu 105 aa N-intein) and a C-terminal intein sequence of 35 amino acid (Mtu 35 aa C-intein). The nucleic acid sequences encoding the Mtu N-intein and the Mtu C-intein can be found in the sequence of Mtu RecA gene (e.g., Accession No. X58485; Perler et al., 1997, Nucl. Acids Res. 25:1087-1093; Davis et al., 1992, Cell 71:201-210; Davis et al., 1991, J. Bacteriol. 173:5653-5662).

In one embodiment, the Mtu 105 aa N-intein is used to prepare the N-intein first antigen recognition portion fragment. The N-terminus of the Mtu 105 aa N-intein is fused to the C-terminus of a C3-like receptor recognition portion, such as but is not limited to an anti-CR1 mAb.

In another embodiment, the Mtu 35 aa C-intein is used to prepare the C-intein second antigen recognition portion fragment. The C-terminus of the Mtu 35 aa C-intein is conjugated with an antigen recognition portion having a Cys at its N-terminus.

In another embodiment of the present invention, a 36 aa C-intein which adds a Cys, Ser, or Thr residue to the C-terminus of the Mtu 35 aa C-intein is used to prepared the C-intein second antigen recognition portion fragment. This 36 aa C-intein can then be conjugated with any antigen recognition moiety, both proteinaceous and non-proteinaceous.

In still another embodiment of the present invention, one or more native proximal N-extein residues are added to the N-terminus of the Mtu 105 aa N-intein to form an N-intein of the invention. In a preferred embodiment, 2 or more native proximal N-extein residues are added to the Mtu 105 aa N-intein. Such N-intein is then used to prepare the N-intein antigen recognition portion fragment.

In still another embodiment of the present invention, one or more native proximal C-extein residues are added to the C-terminus of the Mtu 35 aa C-intein to form a C-intein of the invention. In a preferred embodiment, 3 or more native proximal C-extein residues are added to the Mtu 35 aa C-intein. Such C-intein is then used to prepare C-intein antigen recognition portion fragment.

In still other embodiments, C-inteins comprising 36 to 52 amino acid residues are used to prepare the C-intein second antigen recognition portion fragment. The C-terminus of such a C-intein is conjugated with an antigen recognition portion having a Cys at its N-terminus. Alternatively, C-inteins comprising 36 to 52 amino acid residues plus a Cys, Ser, or Thr at the C-terminus can be used to prepare the C-intein second antigen recognition portion fragment.

In another embodiment, unnatural amino acid residues, such as but is not limited to an amino acid residue containing a caged photoreactive group, such as O-(2-nitrobenzyl) serine, can be incorporated at the N-terminus of an N-intein by site-directed mutagenesis so that splicing reactions can be activated by irradiation of light of an appropriate wavelength, preferably a wavelength in the range of 300-350 nm. Other intein systems that permit controllable trans-splicing can also be designed by various known methods in the art and are considered to be within the scope of the invention.

Nucleic acids encoding the Mtu 105 aa N-intein and any of the modified Mtu N-inteins can be produced by standard methods known in the art. In one embodiment, the nucleic acids encoding an Mtu N-intein is synthesized by annealing a set of oligonucleotides comprising nucleotide sequences that span the nucleotide sequence of the desired N-intein. In another embodiment, the nucleic acids encoding an N-intein can be produced by amplification from an appropriate plasmid, such as but is not limited to the plasmid pMU1B (see Mills et al., 1998, Proc. Natl. Acad. Sci. USA 95:3543-3548). The nucleic acids encoding an N-intein can then be used in the construction of expression vectors.

Nucleic acids encoding the Mtu 35 aa C-intein and any of the modified Mtu C-intein can be produced by standard methods known in the art. In one embodiment, the nucleic acids encoding an Mtu C-intein is synthesized by annealing a set of oligonucleotides comprising nucleotide sequences that span the nucleotide sequence of the desired C-intein. In another embodiment, the nucleic acids encoding a C-intein can be produced by amplification from an appropriate plasmid by standard methods known in the art. The nucleic acids encoding an C-intein can then be used in the construction of expression vectors.

Alternatively, the Mtu N-inteins and C-inteins can be produced by peptide synthesis techniques. Any peptide synthesis techniques can be used for this purpose. It will be recognized by one skilled in the art that a multi-step peptide synthesis can be used for the synthesis of N-inteins. The synthesized N- and C-intein can then be chemically conjugated with antigen recognition portions by any methods known in the art.

5.3. Production and Purification of Bispecific Molecules

The N-intein anti-CR1 fragment and the C-intein antigen recognition portion fragment are produced by fusing appropriate N-intein and C-intein (Section 5.2) with an anti-CR1 and an antigen recognition portion, respectively. The bispecific molecule is then produced by contacting the N-intein anti-CR1 fragment and the C-intein antigen recognition fragment under conditions such that protein trans-splicing occurs. As used herein, "contacting" refers to the placing or mixing of two or more reactant molecules in a reaction buffer, e.g., in a liquid solution, such that the two or more reactant molecules can encounter and react.

5.3.1. Production and Purification of N-intein Fragment

The N-intein anti-CR1 fragment can be produced by conjugating an anti-CR1 with an appropriate N-intein, such as that described in Section 5.2. The N-intein anti-CR1 fragment is preferably produced recombinantly. The N-intein anti-CR1 fragment is then used with an appropriate C-intein antigen recognition portion fragment in a trans-splicing reaction for producing the bispecific molecule.

5.3.1.1. Production of Anti-CR1 Portion

In preferred embodiments, the anti-CR1 portion of the bispecific molecule comprises an anti-CR1 mAb. An anti-CR1 mAb that binds a human C3 receptor can be produced by known methods. In one embodiment, an anti-CR1 mAb, preferably an anti-CR1 IgG, can be prepared using standard hybridoma procedures known in the art (see, for example, Kohler and Milstein, 1975, Nature 256:495-497; Hogg et al., 1983, Eur. J. Immunol. 14:236-243; O'Shea et al., 1985, J. Immunol. 134:2580-2587; Schreiber, U.S. Pat. No. 4,672, 044). A suitable mice is immunized with human CR1 which can be purified from human erythrocytes. The spleen cells obtained from the immunized mice are fused with an immortal mouse myeloma cell line which results in a population of hybridoma cells, including a hybridoma that produces an anti-CR1 antibody. The hybridoma which produces the anti-CR1 antibody is then selected, or 'cloned', from the population of hybridomas using conventional techniques such as enzyme linked immunosorbent assays (ELISA). Hybridoma cell lines expressing anti-CR1 mAb can also be obtained from various sources, for example, the murine anti-CR1 mAb that binds human CR1 described in U.S. Pat. No. 4,672,044 is available as hybridoma cell line ATCC HB 8592 from the American Type Culture Collection (ATCC). Other anti-CR1 mAbs can also be used in the present invention, see, e.g., Nickells et al., 1998, Clin. Exp. Immunol. 112:27-33.

Nucleic acids encoding the heavy and light chains of an anti-CR1 mAb, preferably an anti-CR1 IgG, can then be prepared from the hybridoma cell line by standard methods known in the art. As a non-limiting example, cDNAs encoding the heavy and light chains of the anti-CR1 IgG can be prepared by priming mRNA using appropriate primers, followed by PCR amplification using appropriate forward and reverse primers. Any commercially available kits for cDNA synthesis can be used. The nucleic acids can then be used in the construction of expression vector(s).

In another embodiment, nucleic acids encoding anti-CR1 scFv's are prepared according to standard methods known in the art. In another embodiment, nucleic acids encoding anti-CR1 chimeric antibodies are prepared according to standard methods known in the art (U.S. Pat. Nos. 4,816,567, 4,816,397, 5,693,762; 5,585,089; 5,565,332 and 5,821,337 which are incorporated herein by reference in their entirety). The nucleic acids can then be used in the construction of expression vector(s).

5.3.1.2. Production and Purification of N-intein Anti-CR1 Fragment

In the present invention, an N-intein anti-CR1 fragment can be produced recombinantly, whereby the N-terminus of the nucleotide sequence encoding the N-intein is fused to the C-terminus of the immunoglobulin constant domain sequence. The fusion preferably is with the immunoglobulin heavy chain. However, the fusion with the immunoglobulin light chain is also envisioned. If desired, a nucleotide sequence encoding a suitable linker peptide can also be introduced between the nucleotide sequence encoding the N-intein and the nucleotide sequence encoding the anti-CR1 moiety.

In one embodiment, nucleotide sequence encoding the N-intein anti-CR1 heavy chain fragment and the immunoglobulin light chain are inserted into separate expression vectors, and are co-transfected into a suitable host. Non-limiting examples of hosts include E. coli, yeast, insect cell, and mammalian host systems, such as a Chinese hamster ovary cell line. A mammalian cell line is preferable for the expression of anti-CR1 mAb. Employing separate expression vectors provides for the ability to adjust the proportions of each of the two polypeptide fragments in unequal ratios of the two polypeptide chains, thus providing optimum yields. It is, however, possible to insert the coding sequences for the two polypeptide chains in one expression vector when the expression of at least two polypeptide chains in equal ratios results in high yields or when the ratios are of no particular significance.

In other embodiments, the expression vectors are transfected separately into different hosts. The polypeptides are then mixed in vitro under conditions that allow formation of the multiunit antibody. In another embodiment, the N-intein anti-CR1 heavy chain or the N-intein anti-CR1 light chain is mixed with normal anti-CR1 heavy and light chains such that at least a portion of the multiunit antibodies are N-intein anti-CR1 fragment comprising one N-intein fused to one of the anti-CRI heavy chain or anti-CR1 light chain. This embodiment is therefore useful for producing bispecific molecules comprising an anti-CR1 mAb and one antigen recognition portion fused to the C-terminus of one of the heavy chains or one of the light chains of the anti-CR1 mAb.

In still other embodiments, nucleotide sequence encoding the N-intein scFv fragment is inserted into an expression vector, and transfected into a suitable host. Non-limiting examples of hosts include E. coli, yeast, insect cell, and mammalian host systems, such as a Chinese hamster ovary cell line.

The N-intein anti-CR1 mAb fragment from antibody secreting cells can be purified by various methods known in the art. For example, the N-intein anti-CR1 mAb fragment can be purified by ion exchange chromatography. Non-limiting examples of columns suitable for isolation include DEAE, Hydroxylapatite, Calcium Phosphate (see generally Current Protocols in Immunology, 1993, John Wiley & Sons, Inc., New York, N.Y.). The N-intein anti-CR1 mAb fragment can also be purified by affinity chromatography using a column made of protein A-Sepharose, followed by elution from the immunosorbant using an acid buffer. A column that utilizes C3-like receptor can also be used. One skilled in the art will recognize that any method of purifying proteins using size or affinity will be suitable in the present invention.

5.3.2. Production and Purification C-intein Fragment

The C-intein antigen recognition portion fragment can be produced by conjugating an antigen recognition portion with an appropriate C-intein, such as that described in Section 5.2. The C-intein antigen recognition portion fragment can be produced chemically or recombinantly. The C-intein antigen recognition portion fragment is then mixed with the appropriate N-intein anti-CR1 fragment in a trans-splicing reaction for producing bispecific molecules. Alternatively, a C-intein streptavidin fragment is prepared and mixed with the N-intein fragment in the trans-splicing reaction to produce an anti-CR1 streptavidin molecule, which is then used for producing a bispecific molecule by reacting with a biotinylated antigen recognition portion.

5.3.2.1. Production of Antigen Recognition Moieties

The antigen recognition moiety of the bispecific molecule of the invention can be any molecular moiety that recognizes and binds an antigenic molecule, including but are not limited to any antibody or antigen binding fragments thereof, or any molecular moiety that is recognized and bound by a molecule to be cleared, including but is not limited to an epitope or antigenic determinant, a nucleic acid, and an organic small molecule. Such antigen recognition moieties can be produced by various methods known in the art. The antigen recognition moiety is then conjugated with C-intein for trans-splicing.

Antibodies can be prepared by immunizing a suitable subject with an antigen as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction.

At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein (1975, Nature 256:495-497), the human B cell hybridoma technique by Kozbor et al. (1983, Immunol. Today 4:72), the EBV-hybridoma technique by Cole et al. (1985, Monoclonal Antibodies and Cancer Therapy, Alan R. Liss, Inc., pp. 77-96) or trioma techniques. The technology for producing hybridomas is well known (see generally Current Protocols in Immunology, 1993, John Wiley & Sons, Inc., New York, N.Y.). Hybridoma cells producing a monoclonal antibody of the invention are detected by screening the hybridoma culture supernatants for antibodies that bind the polypeptide of interest, e.g., using a standard ELISA assay.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., 1975, Nature, 256:495, or may be made by recombinant DNA methods (U.S. Pat. No. 4,816,567). The term "monoclonal antibody" as used herein also indicates that the antibody is an immunoglobulin.

In the hybridoma method of generating monoclonal antibodies, a mouse or other appropriate host animal, such as a hamster, is immunized as hereinabove described to elicit lymphocytes that produce or are capable of producing antibodies that will specifically bind to the protein used for immunization (see generally, U.S. Pat. No. 5,914,112, which is incorporated herein by reference in its entirety.)

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA.

Human myeloma and mouse-human heteromyeloma cell lines also have been described for the production of human monoclonal antibodies (Kozbor, 1983, J. Immunol., 133:3001; Brodeur et al., Monoclonal Antibody Production Techniques and Applications, pp. 51-63 (Marcel Dekker, Inc., New York, 1987)). Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immuno-absorbent assay (ELISA). The binding affinity of the monoclonal antibody can, for example, be determined by the Scatchard analysis of Munson et al., 1980, Anal. Biochem., 107:220.

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Alternative to preparing monoclonal antibody-secreting hybridomas, a monoclonal antibody directed against a pathogen or pathogenic antigenic molecule polypeptide of the invention can be identified and isolated by screening a recombinant combinatorial immunoglobulin library (e.g., an antibody phage display library) with the antigen of interest. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734. A phage display library permits selection of desired antibody or antibodies from a very large repertoire of specificities. An additional advantage of a phage display library is that the nucleic acids encoding the selected antibodies can be obtained conveniently, thereby facilitating subsequent construction of expression vectors.

In addition, techniques developed for the production of "chimeric antibodies" (Morrison et al., 1983, Proc. Natl. Acad. Sci., 81, 6851-6855; Neuberger et al., 1983, Nature 312, 604-608; Takeda et al., 1985, Nature, 314, 452-454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

Humanized antibodies are antibody molecules from non-human species having one or more complementarity determining regions (CDRS) from the non-human species and a framework region from a human immunoglobulin molecule. (see e.g., U.S. Pat. No. 5,585,089, which is incorporated herein by reference in its entirety.) Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,493; PCT Publication No. WO 86/01533; U.S. Pat. Nos. 4,816,567 and 5,225,539; European Patent Application 125,023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314:446-449; Shaw et al., 1988, J. Natl. Cancer Inst. 80:1553-1559; Morrison 1985, Science 229:1202-1207; Oi et al., 1986, Bio/Techniques 4:213; Jones et al., 1986, Nature 321:552-525; Verhoeyan et al., 1988, Science 239:1534; and Beidler et al., 1988, J. Immunol. 141: 4053-4060.

Complementarity determining region (CDR) grafting is another method of humanizing antibodies. It involves reshaping murine antibodies in order to transfer full antigen specificity and binding affinity to a human framework (Winter et al. U.S. Pat. No. 5,225,539). CDR-grafted antibodies have been successfully constructed against various antigens, for example, antibodies against IL-2 receptor as described in Queen et al., 1989 (Proc. Natl. Acad. Sci. USA 86:10029); antibodies against cell surface receptors-CAMPATH as described in Riechmann et al. (1988, Nature, 332:323); antibodies against hepatitis B in Cole et al. (1991, Proc. Natl. Acad. Sci. USA 88:2869); as well as against viral antigens-respiratory syncitial virus in Tempest et al. (1991, Bio-Technology 9:267). CDR-grafted antibodies are generated in which the CDRs of the murine monoclonal antibody are grafted into a human antibody. Following grafting, most antibodies benefit from additional amino acid changes in the framework region to maintain affinity, presumably because framework residues are necessary to maintain CDR conformation, and some framework residues have been demonstrated to be part of the antigen binding site. However, in order to preserve the framework region so as not to introduce any antigenic site, the sequence is compared with established germline sequences followed by computer modeling.

Completely human antibodies are particularly desirable for therapeutic treatment of human patients. Such antibodies can be produced using transgenic mice which are incapable of expressing endogenous immunoglobulin heavy and light chain genes, but which can express human heavy and light chain genes. The transgenic mice are immunized in the normal procedure, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

An antigenic fragment suitable for use as an antigenic recognition moiety comprises at least a portion of the antigen that is 8 amino acids, more preferably 10 amino acids and more preferably still, 15 amino acids long. Antigens and antigenic fragments used as antigen recognition moieties can be recombinantly expressed or chemically synthesized.

The invention also provides chimeric or fusion antigens for use as antigen recognition moieties. As used herein, a "chimeric antigen" or "fusion antigen" comprises all or part of an antigen for use in the invention, operably linked to a heterologous polypeptide. Within the fusion antigen, the term "operably linked" is intended to indicate that the antigen and the heterologous polypeptide are fused in-frame to each other. The heterologous polypeptide can be fused to the N-terminus or C-terminus of the antigen.

Chimeric and fusion proteins can be produced by standard recombinant DNA techniques. In one embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (e.g., Ausubel et al., supra). Moreover, many expression vectors are commercially available that already encode a fusion domain (e.g., a GST polypeptide). A nucleic acid encoding an immunogen can be cloned into such an expression vector such that the fusion domain is linked in-frame to the polypeptide.

Other types of antigen recognition moiety can be produced using appropriate methods known in the art. For example, nucleic acids can be produced by any known DNA synthesis methods. Organic small molecules can be produced by organic synthesis.

5.3.2.2. Production and Purification of C-intein Antigen Recognition Portion Fragment In the present invention, a C-intein antigen recognition portion fragment is produced recombinantly, whereby the C-terminus of the nucleotide sequence encoding the C-intein is fused to the N-terminus of an antigen recognition moiety. If desired, a nucleotide sequence encoding a suitable linker peptide can also be introduced between the nucleotide sequence encoding the C-intein and the nucleotide sequence encoding the antigen recognition moiety.

In one embodiment, nucleotide sequence encoding a C-intein antigen recognition portion fragment is inserted into a suitable expression vector, and are transfected into a suitable host. Non-limiting example include E. coli, yeast, insect cell, and mammalian systems, such as a Chinese hamster ovary cell line.

The C-intein antigen recognition portion fragment from antibody secreting cells can be isolated by ion exchange chromatography. Non-limiting examples of columns suitable for purification of the bispecific antibodies of the invention include DEAE, Hydroxylapatite, Calcium Phosphate (see generally Current Protocols in Immunology, 1993, John Wiley & Sons, Inc., New York, N.Y.). The C-intein antigen recognition portion fragment can also be purified by affinity chromatography using a suitable column that uses the specific antigen. One skilled in the art will recognize that any method of purifying proteins using size or affinity will be suitable in the present invention.

A C-intein antigen recognition portion fragment can also be produced by chemically conjugating C-intein and the desired antigen recognition moiety. If desired, a suitable linker peptide, such as but is not limited to a peptide linker or a PEG linker, can also be introduced between the C-intein and the antigen recognition moiety.

A C-intein can also be conjugated with a streptavidin molecule. In one embodiment, a C-intein is conjugated with a streptavidin chemically by standard methods known in the art. For example, the streptavidin can be conjugated to the C-intein via a thioether linker (see, for example, Li et al., 1999, Protein Engineering 12:787-796).

In another embodiment, a C-intein is conjugated with streptavidin recombinantly. Nucleic acid encoding a C-intein is fused to the nucleic acid encoding the monomer of core streptavidin and inserted into an appropriate vector which can then be expressed in an appropriate host. It is known, however, that streptavidin can form tetramers and dimers (Ernst et al., 1999, Human Antibodies 9:165-170; Kipriyznov et al., 1996, Protein Engineering 9:203-211). It may therefore be desirable to dissociate such tetramers and dimers using any methods known in the art. In one embodiment, streptavidin multimers are first denatured in a suitable denaturant, such as but is not limited to urea. The denatured proteins are then diluted to an appropriate concentration and allowed to refold into monomers.

Certain C-inteins, such as the engineered Mtu 35 aa C-intein, may misfold and form aggregate. This can normally be remedied by solubilizing and purifying the C-intein fragment in a suitable denaturant, such as but is not limited to urea. The denatured C-intein fragment can then be mixed with the N-intein fragment for reconstitution and trans-splicing.

5.3.3. Reconstitution and Trans-splicing

In vitro trans-splicing can be carried out by adding the purified C-intein antigen recognition portion fragment to the purified N-intein anti-CR1 fragment in an appropriate reaction buffer. The reaction mixture is incubated at an appropriate temperature for an appropriate amount of time. The reaction temperature and incubation time depend in part on the specific trans-splicing system used and can be determined by one skilled in the art by standard methods, including but is not limited to monitoring the progress of the reaction by analyzing the reaction mixture by size exclusion HPLC or SDS-PAGE.

The concentrations of the intein fragments, i.e., the N-intein anti-CR1 and C-intein antigen recognition portion, can be adjusted for higher splicing efficiency and optimum reaction yield. Any methods known in the art can be used to determined the concentrations of proteins, such as but is not limited to the bichinchoninic acid method using BSA as standard (Smith et al., 1985, Anal. Biochem. 150:76-85). Normally, higher reactant concentrations is advantageous for increased yield. For certain split intein systems, however, higher reactant concentrations may lead to the formation of aggregates and the precipitation of one or both intein fragments. Under such circumstances, the concentration of one or both intein fragments can be optimized in small scale experiments before the production of the bispecific molecule. The concentrations of the intein fragments can also be adjusted such that the concentration of one intein fragment is higher than the other. This may be particularly useful when one of the intein fragment is more difficult and/or more expensive to produce. A higher concentration of one intein fragment permits more efficient use of the other intein fragment. In some embodiments of the invention, it may be desirable to conjugate two different antigen recognition portion to the two heavy or light chains of an anti-CR1 mAb. In such instances, the concentrations of the N-intein anti-CR1 fragment and the two C-intein antigen recognition portion fragments can be adjusted according to the relative efficiency of the two trans-splicing reactions such that the yield for the desired bispecific molecule is optimized.

In cases where certain C-inteins, such as the engineered Mtu 35 aa C-intein, may misfold and form an aggregate, reconstitution can be carried out in a suitable denaturant, such as but is not limited to urea. The denaturant is then removed by methods known in the art, such as but is not limited to dialysis against a suitable buffer, to allow renaturation and trans-splicing.

Bispecific molecules can be purified by methods known to one skilled in the art using molecular size or specific binding affinity or a combination thereof. In one embodiment, the bispecific molecules can be purified by ion exchange chromatography using columns suitable for isolation of the bispecific molecules of the invention including DEAE, Hydroxylapatite, Calcium Phosphate (see generally Current Protocols in Immunology, 1993, John Wiley & Sons, Inc., New York, N.Y.).

In another embodiment, bispecific molecules are purified by three-step successive affinity chromatography (Corvalan and Smith, 1987, Cancer Immunol. Immunother., 24:127-132): the first column is made of protein A bound to a solid matrix, wherein the Fc portion of the antibody binds protein A, and wherein the antibodies bind the column; followed by a second column that utilizes C3-like receptor bound to a solid matrix which assays for C3-like receptor binding via the anti-CR1 mAb portion of the bispecific molecule; and followed by a third column that utilizes specific binding of an antigenic molecule of interest which binds the antigen recognition portion of the bispecific molecule.

The bispecific molecules can also be purified by a combination of size exclusion HPLC and affinity chromatography. In one embodiment, the appropriate fraction eluted from size exclusion HPLC is further purified using a column containing an antigenic molecule specific to the antigen recognition portion of the bispecific molecule.

The bispecific molecules may also be isolated by isoelectric focusing of antibodies.

The bispecific molecules can be characterized by various methods known in the art. In one embodiment, the bispecific molecules can be characterized by SDS-PAGE and Western blot. The molecular weight of the bispecific molecule is determined by SDS-PAGE. The bispecificity of the molecules in the appropriate band is then determined by Western blots using both CR1 and the antigenic molecule of interest. Alternatively, the bispecifity of the molecules can be determined by solid-phase immunoassays, such as enzyme-linked immunosorbent assays (ELISA). The structure of the bispecific molecule may further be verified by selective sequencing of the linker region of the proteolyzed bispecific molecule.

5.3.4. Production of Bispecific Molecules Containing a Streptavidin-biotin Linker Bispecific molecules comprising a streptavidin-biotin linker are produced using anti-CR1-streptavidin and biotinylated antigen recognition moiety. Any standard methods known in the art can be used to prepare the biotinylated antigen recognition moiety.

This configuration of the invention is particularly useful in producing bispecific molecules that comprises a mAb as the second antigen recognition portion that is conjugated to a C3-like receptor recognition portion. Direct conjugation of an antigen recognition mAb using trans-splicing results a bispecific molecule wherein the amino terminus of the antigen recognition mAb is fused to the carboxy terminus of the anti-CR1 portion. The antigen binding affinity of this bispecific molecule may be compromised. On the other hand, it is known that biotinylation leads to negligible modification of the protein with retention of immunoreactivity (Foulon et al., 1999, Bioconjugate Chem. 10:867-876; Khawli et al., 1993, Antibody, Immunoconjugates, Radiopharm. 6:13-27). Thus, using the streptavidin-biotin configuration of the invention offers a means to produce a bispecific molecule that comprises a mAb as the second antigen recognition portion. A mAb can be conjugated with biotin using various activated biotin agents, including but is not limited to NHS-LC-biotin. The biotin is preferably conjugated with a residue away from the antigen recognition domains of the mAb such that the antigen binding capability of the mAb and the bispecific molecule produced from the mAb is not impaired. For example, the biotin may be conjugated with the ε-amino group of a lysine residue. More preferably, the biotin is conjugated with a residue near the carboxy terminus of the mAb. Biotinylated mAbs and bispecific molecules produced therefrom can be screened for functional antigen binding capabilities using any method that assays specific binding of an antigenic molecule which binds the antigen recognition portion of the mAb or the bispecific molecule. This configuration of the invention can also be used in producing bispecific molecules from pre-existing antibodies.

This configuration of the invention is also particularly useful in producing a bispecific molecule that comprises a non-proteinaceous antigen recognition moiety that is conjugated to a C3-like receptor recognition portion, such as but is not limited to a nucleic acid. In one embodiment, a desired nucleic acid is amplified using a PCR primer containing a suitable restriction digestion site which, when cleaved by a restriction endonuclease, leaves an overhanging terminus. A biotinylated nucleotide, such as but is not limited to a biotinyl-dUTP, is then incorporated at the terminus using a DNA polymerase, such as but is not limited to DNA polymerase Klenow fragment (see, for example, U.S. Pat. No. 6,060,596). Methods for producing other biotinylated antigen recognition moieties will be recognized by one skilled in the art when a antigen recognition moiety is provided.

The biotinylated antigen recognition moiety can then be conjugated with the anti-CR1 portion of the bispecific molecule via a streptavidin-biotin linkage.

5.3.5. In Vivo Production of Bispecific Molecules

Bispecific molecules can also be produced in vivo. In one embodiment of the invention, bispecific molecules are produced in a suitable host cell. Nucleotide sequences encoding the N-intein anti-CR1 heavy chain fragment and the immunoglobulin light chain and the C-intein antigen recognition portion fragment are inserted into separate expression vectors, and are co-transfected into the host cell. Non-limiting examples of hosts include E. coli, yeast, insect cell, and mammalian host systems, such as a Chinese hamster ovary cell line. A mammalian cell line is preferable for the expression of anti-CR1 mAb. Employing separate expression vectors provides for the ability to adjust the proportions of each of the three polypeptide fragments in unequal ratios of the three polypeptide chains, thus providing optimum yields. In another embodiment, nucleotide sequences encoding the N-intein anti-CR1 heavy chain fragment and the immunoglobulin light chain and the C-intein antigen recognition portion fragment are inserted in one expression vector. The transfected cells can be induced to express the proteins by standard methods known in the art. Bispecific molecules can be purified by standard methods known in the art.

5.4 Production of Polyclonal Libraries of Bispecific Molecules Using Protein Trans-splicing Protein trans-splicing can also be used for producing libraries of bispecific molecules comprising a plurality of bispecific molecules with different antigen recognition specificities. Particularly of interest are polyclonal libraries wherein the plurality of antigen recognition portions has specificities for multiple epitopes of a targeted antigenic molecule and/or multiple variants of a targeted antigenic molecule. Such polyclonal libraries of bispecific molecules can be used for more efficient clearance of pathogens that have multiple epitopes and/or pathogens that have multiple variants or mutants, which normally cannot be effectively targeted and cleared by a monoclonal antibody having a single specificity. By targeting multiple epitopes and/or multiple variants of a pathogen, the polyclonal library of bispecific molecules is advantageous in the clearance of pathogens that have a higher mutation rate because simultaneous mutations at more than one epitopes tend to be much less frequent.

In a preferred embodiment, nucleic acid encoding the C-intein of a split intein is recombinantly fused by any standard methods known in the art to the nucleic acid encoding a polypeptide antibody in a member of a phage display library such that the fused nucleic acid encodes a C-intein-polypeptide in which the N-terminus of the C-intein is fused to the C-terminus of the polypeptide antibody, thereby obtaining a phage display library displaying a repertoire of C-intein-polypeptides. Preferably, the number of specificities of such phage display library is near the number of different specificities that are expressed at any one time by lymphocytes of the immune system of a mammal, e.g., $10^7$ (or $10^6$ to $10^8$) different specificities by the murine immune system (see, e.g., Milstein, 1990, Proc. R. Soc. London B239:1-16). More preferably the number of specificities of the phage display library is higher than the number of different specificities that are expressed at any one time by lymphocytes of the immune system of a mammal. Most preferably the phage display library comprises the complete set of specificities that can be expressed by lymphocytes. Polyclonal C-intein antibody fusion proteins can then be obtained by affinity screening of the phage display library with an antigen of interest. Kits for generating and screening phage display libraries are commercially available (e.g., Pharmacia Recombinant Phage Antibody System, Catalog No. 27-9400-01; and the Stratagene antigen SurfZAP™ Phage Display Kit, Catalog No. 240612). Additionally, examples of methods and reagents particularly amenable for use in generating and screening antibody display library can be found in, for example, U.S. Pat. Nos. 5,223,409 and 5,514,548; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al., 1991, Bio/Technology 9:1370-1372; Hay et al., 1992, Hum. Antibod. Hybridomas 3:81-85; Huse et al., 1989, Science 246:1275-1281; Griffiths et al., 1993, EMBO J. 12:725-734.

In other embodiments, polyclonal antibodies can be obtained by affinity screening of an antibody phage display library having a sufficiently large and diverse repertoire of specificities with an antigen of interest before recombinant fusion with a C-intein. The nucleic acid encoding each member of the selected antibodies is then fused to a C-intein of a suitable trans-splicing system and expressed in a suitable host. The C-intein antigen recognition portion fragments are allowed to reconstitute with the corresponding N-intein anti-CR1 fragments and undergo trans-splicing reactions.

In a preferred embodiment, the polyclonal library of bispecific molecules is produced using the whole collection of selected displayed antibodies without clonal isolation of individual members. The method for producing a polyclonal library of antibodies from a phage display library without clonal isolation is described in U.S. Pat. No. 6,057,098, which is incorporated by reference herein in its entirety. Polyclonal antibodies are obtained by affinity screening of a phage display library having a sufficiently large repertoire of specificities with an antigenic molecule having multiple epitopes, preferably after enrichment of displayed library members that display multiple antibodies. The nucleic acids encoding the selected display antibodies are excised and amplified using suitable PCR primers. The nucleic acids can be purified by gel electrophoresis such that the full length nucleic acids are isolated. Each of the nucleic acids is then fused to a C-intein of an appropriate trans-splicing system such that a population of expression vectors having different inserts is obtained. The population of expression vectors is then expressed in a suitable host or hosts. The population of C-intein antigen recognition fragments is then mixed with the N-intein anti-CR1 fragments to produce a library of bispecific molecules having a plurality of specificities.

In another preferred embodiment, the polyclonal library of bispecific molecules is produced from a population of displayed antibodies obtained by affinity screening with a set of antigens, such as but are not limited to a set of variants of a pathogen and/or a mixture of various pathogens. Such polyclonal library of bispecific molecules can be used to target and clear a set of antigens.

In still another preferred embodiment, the polyclonal library of bispecific molecules is produced using trans-splicing and a streptavidin-biotin linker. The plurality of antibodies is selected and produced by standard phage display procedure and is biotinylated. The plurality of biotinylated antibodies is then conjugated with anti-CR1 streptavidin molecules prepared by trans-splicing.

In still another preferred embodiment, a plurality of N-intein anti-CR1 mAb fragments comprising a plurality of anti-CR1 mAbs that target different sites on CR1 molecules of the red blood cells are mixed with the plurality of C-intein antigen recognition fragments with a plurality of specificities to produce a polyclonal library of bispecific molecules having polyclonal first and second antigen recognition portions.

Although polyclonal libraries of bispecific molecules produced from phage display libraries are described, it will be recognized by one skilled in the art that the plurality of second antigen recognition portions used in the generation of a library can be obtained from any population of suitable antigen recognition moieties. Libraries of bispecific molecules produced from such population of antigen recognition moieties are intended to be within the scope of the invention.

5.5. Uses of Bispecific Molecules

The bispecific molecules of the present invention are useful in treating or preventing a disease or disorder associated with the presence of a pathogenic antigenic molecule. The pathogenic antigenic molecule can be any substance that is present in the circulation that is potentially injurious to or undesirable in the subject to be treated, including but are not limited to proteins or drugs or toxins, autoantibodies or autoantigens, or a molecule of any infectious agent or its products. A pathogenic antigenic molecule is any molecule containing an antigenic determinant (or otherwise capable of being bound by a binding domain) that is or is part of a substance (e.g., a pathogen) that is the cause of a disease or disorder or any other undesirable condition.

The preferred subject for administration of a bispecific antibody of the invention, for therapeutic or prophylactic purposes, is a mammal including but not limited to non-human animals (e.g., horses, cows, pigs, dogs, cats, sheep, goats, mice, rats, etc.), and in a preferred embodiment, is a human or non-human primate.

Circulating pathogenic antigenic molecules cleared by the fixed tissue phagocytes include any antigenic moiety that is harmful to the subject. Examples of harmful pathogenic antigenic molecules include any pathogenic antigenic molecule associated with a parasite, fungus, protozoa, bacteria, or virus. Furthermore, circulating pathogenic antigenic molecules may also include toxins, immune complexes, autoantibodies, drugs, an overdose of a substance, such as a barbiturate, or anything that is present in the circulation and is undesirable or detrimental to the health of the host mammal. Failure of the immune system to effectively remove the pathogenic antigenic molecules from the mammalian circulation can lead to traumatic and hypovolemic shock (Altura and Hershey, 1968, Am. J. Physiol. 215:1414-9).

Moreover, non-pathogenic antigens, for example transplantation antigens, are mistakenly perceived to be harmful to the host and are attacked by the host immune system as if they were pathogenic antigenic molecules. The present invention further provides an embodiment for treating transplantation rejection comprising administering to a subject an effective amount of a bispecific antibody that will bind and remove immune cells or factors involved in transplantation rejection, e.g., transplantation antigen specific antibodies.

5.5.1 Autoimmune Antigens

In one embodiment, the pathogenic antigenic molecule to be cleared from the circulation includes autoimmune antigens. These antigens include but are not limited to autoantibodies or naturally occurring molecules associated with autoimmune diseases.

As one example, certain humans with hemophilia have been shown to be deficient in factor VIII. Recombinant factor VIII replacement treats this hemophilia. However, eventually some patients develop antibodies against factor VIII, thus interfering with the therapy. The bispecific antibodies of the present invention prepared with an anti-anti-factor VIII antibody provides a therapeutic solution for this problem. In particular, a bispecific antibody with specificity of the first antigen recognition portion to a C3-like receptor and specificity of the second antigen recognition portion to an anti-factor VIII autoantibody would be therapeutically useful in clearing the autoantibodies from the circulation, thus, ameliorating the disease.

Further examples of autoantibodies which can be cleared by the bispecific antibodies of the present invention include, but are not limited to, autoantibodies to the following antigens: the muscle acetylcholine receptor (the antibodies are associated with the disease myasthenia gravis); cardiolipin (associated with the disease lupus); platelet associated proteins (associated with the disease idiopathic thrombocytopenic purpurea); the multiple antigens associated with Sjogren's Syndrome; the antigens implicated in the case of tissue transplantation autoimmune reactions; the antigens found on heart muscle (associated with the disease autoimmune myocarditis); the antigens associated with immune complex mediated kidney disease; the dsDNA and ssDNA antigens (associated with lupus nephritis); desmogleins and desmoplakins (associated with pemphigus and pemphigoid); or any other antigen which is characterized and is associated with disease pathogenesis.

When the above bispecific antibodies are injected into the circulation of a human or non-human primate, the bispecific antibodies will bind to red blood cells via the human or primate C3 receptor domain recognition site, at a high percentage and in agreement with the number of C3-like receptor sites on red blood cells. The bispecific antibodies will simultaneously associate with the autoantibody indirectly, through the antigen, which is bound to the monoclonal antibody. The red blood cells which have the bispecific antibody/autoantibody complex on their surface then facilitate the neutralization and clearance from the circulation of the bound pathogenic autoantibody.

In the present invention, the bispecific antibodies facilitate pathogenic antigen or autoantibody binding to hematopoietic cells expressing a C3-like receptor on their surface and subsequently clear the pathogenic antigen or autoantibody from the circulation, without also clearing the hematopoietic cells.

5.5.2 Infectious Diseases

In specific embodiments, infectious diseases are treated or prevented by administration of a bispecific molecule that binds both an antigen of an infectious disease agent and a C3-like receptor. Thus, in such an embodiment, the pathogenic antigenic molecule is an antigen of an infectious disease agent.

Such antigen can be but is not limited to: influenza virus hemagglutinin (Genbank accession no. JO2132; Air, 1981, Proc. Natl. Acad. Sci. USA 78:7639-7643; Newton et al., 1983, Virology 128:495-501), human respiratory syncytial virus G glycoprotein (Genbank accession no. Z33429; Garcia et al., 1993, J. Virol.; Collins et al., 1983, Proc. Natl. Acad. Sci. USA 81:7683), core protein, matrix protein or other protein of Dengue virus (Genbank accession no. M19197; Hahn et al., 1988, Virology 162:167-180), measles virus hemagglutinin (Genbank accession no. M81899; Rota et al., 1992, Virology 188:135-142), herpes simplex virus type 2 glycoprotein gB (Genbank accession no. M14923; Bzik et al., 1986, Virology 155:322-333), poliovirus I VP1 (Emini et al., 1983, Nature 304:699), envelope glycoproteins of HIV I (Putney et al., 1986, Science 234:1392-1395), hepatitis B surface antigen (Itoh et al., 1986, Nature 308:19; Neurath et al., 1986, Vaccine 4:34), diphtheria toxin (Audibert et al., 1981, Nature 289:543), streptococcus 24M epitope (Beachey, 1985, Adv. Exp. Med. Biol. 185:193), gonococcal pilin (Rothbard and Schoolnik, 1985, Adv. Exp. Med. Biol. 185:247), pseudorabies virus g50 (gpD), pseudorabies virus II (gpB), pseudorabies virus gIII (gpC), pseudorabies virus glycoprotein H, pseudorabies virus glycoprotein E, transmissible gastroenteritis glycoprotein 195, transmissible gastroenteritis matrix protein, swine rotavirus glycoprotein 38, swine parvovirus capsid protein, Serpulina hydodysenteriae protective antigen, bovine viral diarrhea glycoprotein 55, Newcastle disease virus hemagglutinin-neuraminidase, swine flu hemagglutinin, swine flu neuraminidase, foot and mouth disease virus, hog colera virus, swine influenza virus, African swine fever virus, Mycoplasma hvopneumoniae, infectious bovine rhinotracheitis virus (e.g., infectious bovine rhinotracheitis virus glycoprotein E or glycoprotein G), or infectious laryngotracheitis virus (e.g. , infectious laryngotracheitis virus glycoprotein G or glycoprotein I), a glycoprotein of La Crosse virus (Gonzales-Scarano et al., 1982, Virology 120: 42), neonatal calf diarrhea virus (Matsuno and Inouye, 1983, Infection and Immunity 39:155), Venezuelan equine encephalomyelitis virus (Mathews and Roehrig, 1982, J. Immunol. 129:2763), punta toro virus (Dalrymple et al., 1981, Replication of Negative Strand Viruses, Bishop and Compans (eds.), Elsevier, N.Y., p. 167), murine leukemia virus (Steeves et al., 1973, J. Virol. 14:187), mouse mammary tumor virus (Massey and Schochetman, 1981, Virology 115: 20), hepatitis B virus core protein and/or hepatitis B virus surface antigen or a fragment or derivative thereof (see, e.g., U.K. Patent Publication No. GB 2034323A published Jun. 4, 1980; Ganem and Varmus, 1987, Ann. Rev. Biochem. 56:651-693; Tiollais et al., 1985, Nature 317:489-495), of equine influenza virus or equine herpesvirus (e.g., equine influenza virus type A/Alaska 91 neuraminidase, equine influenza virus type A/Miami 63 neuraminidase, equine influenza virus type A/Kentucky 81 neuraminidase equine herpesvirus type 1 glycoprotein B, and equine herpesvirus type 1 glycoprotein D, antigen of bovine respiratory syncytial virus or bovine parainfluenza virus (e.g., bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase), bovine viral diarrhea virus glycoprotein 48 or glycoprotein 53.

Additional diseases or disorders that can be treated or prevented by the use of a bispecific molecule of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, hantavirus, coxsachie virus, mumps virus, measles virus, rubella virus, polio virus, human immunodeficiency virus type I (HIV-I), and human immunodeficiency virus type II (HIV-II), any picornaviridae, enteroviruses, caliciviridae, any of the Norwalk group of viruses, togaviruses, such as Dengue virus, alphaviruses, flaviviruses, coronaviruses, rabies virus, Marburg viruses, ebola viruses, parainfluenza virus, orthomyxoviruses, bunyaviruses, arenaviruses, reoviruses, rotaviruses, orbiviruses, human T cell leukemia virus type I, human T cell leukemia virus type II, simian immunodeficiency virus, lentiviruses, polyomaviruses, parvoviruses, Epstein-Barr virus, human herpesvirus-6, cercopithecine herpes virus 1 (B virus), and poxviruses.

Bacterial diseases or disorders that can be treated or prevented by the use of bispecific molecules of the present invention include, but are not limited to, Mycobacteria rickettsia, Mycoplasma, Neisseria spp. (e.g., Neisseria menigitidis and Neisseria gonorrhoeae), Legionella, Vibrio cholerae, Streptococci, such as Streptococcus pneumoniae, Corynebacteria diphtheriae, Clostridium tetani, Bordetella pertussis, Haemophilus spp. (e.g., influenzae), Chlamydia spp., enterotoxigenic Escherichia coli, and Bacillus anthracis (anthrax), etc.

Protozoal diseases or disorders that can be treated or prevented by the use of bispecific molecules of the present invention include, but are not limited to, plasmodia, eimeria, Leishmania, and trypanosoma.

5.5.3 Additional Pathogenic Antigenic Molecules

In one embodiment, the pathogenic antigenic molecule to be cleared from the circulation by the methods and compositions of the present invention encompass any serum drug, including but is not limited to barbiturates, tricyclic antidepressants, and Digitalis.

In another embodiment, the pathogenic antigenic molecule to be cleared includes any serum antigen that is present as an overdose and can result in temporary or permanent impairment or harm to the subject. This embodiment particularly relates to drug overdoses.

In another embodiment, the pathogenic antigenic molecule to be cleared from the circulation include naturally occurring substances. Examples of naturally occurring pathogenic antigenic molecules that could be removed by the methods and compositions of the present invention include but are not limited to low density lipoproteins, interleukins or other immune modulating chemicals and hormones.

5.5.4. Cocktails of Bispecific Molecules

Various purified bispecific molecules can be combined into a "cocktail" of bispecific molecules. Such cocktail of bispecific molecules can include bispecific molecules having an anti-CR1 mAb as the first antigen recognition portion and any one of several desired antigen recognition moieties as the second antigen recognition portion. For example, the bispecific molecule cocktail comprises a plurality of different bispecific molecules, wherein each different bispecific molecule in the plurality contains a different second antigen recognition portion that targets a different pathogens; the second antigen recognition portions can be proteinaceous and/or non-proteinaceous moieties. Such bispecific molecule cocktails are useful as personalized medicine tailored according to the need of individual patients.

5.5.5. Dose of Bispecific Antibodies

The dose can be determined by a physician upon conducting routine experiments. Prior to administration to humans, the efficacy is preferably shown in animal models. Any animal model for a circulatory disease known in the art can be used.

More particularly, the dose of the bispecific antibody can be determined based on the hematopoietic cell concentration and the number of C3-like receptor epitope sites bound by the anti-C3-like receptor monoclonal antibodies per hematopoietic cell. If the bispecific antibody is added in excess, a fraction of the bispecific antibody will not bind to hematopoietic cells, and will inhibit the binding of pathogenic antigens to the hematopoietic cell. The reason is that when the free bispecific antibody is in solution, it will compete for available pathogenic antigen with bispecific antibody bound to hematopoietic cells. Thus, the bispecific antibody-mediated binding of the pathogenic antigens to hematopoietic cells follows a bell-shaped curve when binding is examined as a function of the concentration of the input bispecific antibody concentration.

Viremia may result in up to $10^8$-$10^9$ viral particles/ml of blood (HIV is $10^6$/ml; (Ho, 1997, J. Clin. Invest. 99:2565-2567)); the dose of therapeutic bispecific antibodies should preferably be, at a minimum, approximately 10 times the antigen number in the blood.

In general, for antibodies, the preferred dosage is 0.1 mg/kg to 100 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). A method for lipidation of antibodies is described by Cruikshank et al. ((1997) J. Acquired Immune Deficiency Syndromes and Human Retrovirology 14:193).

As defined herein, a therapeutically effective amount of bispecific antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but is not limited to the severity of the disease or disorder, previous treatments, the general health and/or age of the subject, and other diseases present. Moreover, treatment of a subject with a therapeutically effective amount of a bispecific antibody can include a single treatment or, preferably, can include a series of treatments. In a preferred example, a subject is treated with a bispecific antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a bispecific antibody, used for treatment may increase or decrease over the course of a particular treatment. Changes in dosage may result and become apparent from the results of diagnostic assays as described herein.

It is understood that appropriate doses of bispecific antibody agents depends upon a number of factors within the ken of the ordinarily skilled physician, veterinarian, or researcher. The dose(s) of the bispecific antibody will vary, for example, depending upon the identity, size, and condition of the subject or sample being treated, further depending upon the route by which the composition is to be administered, if applicable, and the effect which the practitioner desires the bispecific antibody to have upon a pathogenic antigenic molecule or autoantibody.

It is also understood that appropriate doses of bispecific antibodies depend upon the potency of the bispecific antibody with respect to the antigen to be cleared. Such appropriate doses may be determined using the assays described herein. When one or more of these bispecific antibodies is to be administered to an animal (e.g., a human) in order to clear an antigen, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the bispecific antibody employed, the age, body weight, general health, gender, and diet of the subject, the time of administration, the route of administration, the rate of excretion, any drug combination, and the concentration of antigen to be cleared.

5.5.6. Pharmaceutical Formulation and Administration

The bispecific antibodies of the invention can be incorporated into pharmaceutical compositions suitable for administration. Such compositions typically comprise bispecific antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the bispecific antibody, use thereof in the compositions is contemplated. Supplementary bispecific antibodies can also be incorporated into the compositions.

A pharmaceutical composition of the invention is formulated to be compatible with its intended route of administration. The preferred route of administration is intravenous. Other examples of routes of administration include parenteral, intradermal, subcutaneous, transdermal (topical), and transmucosal. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™

(BASF; Parsippany, N.J.) or phosphate buffered saline (PBS). In all cases, the composition must be sterile and should be fluid to the extent that the viscosity is low and the bispecific antibody is injectable. It must be stable under the conditions of manufacture and storage and must be preserved against the contaminating action of microorganisms such as bacteria and fungi.

The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the bispecific antibody (e.g., one or more bispecific antibodies) in the required amount in an appropriate solvent with one or a combination of ingredients enumerated above, as required, followed by filtered sterilization. Generally, dispersions are prepared by incorporating the bispecific antibody into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

In one embodiment, the bispecific antibodies are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811 which is incorporated herein by reference in its entirety.

It is advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of bispecific antibody calculated to produce the desired therapeutic effect in association with the required pharmaceutical carrier. The specification for the dosage unit forms of the invention are dictated by and directly dependent on the unique characteristics of the bispecific antibody and the particular therapeutic effect to be achieved, and the limitations inherent in the art of compounding such a bispecific antibody for the treatment of individuals.

The pharmaceutical compositions can be included in a kit, in a container, pack, or dispenser together with instructions for administration.

5.5.7. Ex Vivo Preparation of the Bispecific Molecule

In an alternative embodiment, the bispecific molecule, such as a bispecific antibody, is prebound to hematopoietic cells of the subject ex vivo, prior to administration. For example, hematopoietic cells are collected from the individual to be treated (or alternatively hematopoietic cells from a non-autologous donor of the compatible blood type are collected) and incubated with an appropriate dose of the therapeutic bispecific antibody for a sufficient time so as to allow the antibody to bind the C3-like receptor on the surface of the hematopoietic cells. The hematopoietic cell/bispecific antibody mixture is then administered to the subject to be treated in an appropriate dose (see, for example, Taylor et al., U.S. Pat. No. 5,487,890).

The hematopoietic cells are preferably blood cells, most preferably red blood cells.

Accordingly, in a specific embodiment, the invention provides a method of treating a mammal having an undesirable condition associated with the presence of a pathogenic antigenic molecule, comprising the step of administering a hematopoietic cell/bispecific molecule complex to the subject in a therapeutically effective amount, said complex consisting essentially of a hematopoietic cell expressing a C3-like receptor bound to one or more bispecific molecules. The method alternatively comprises a method of treating a mammal having an undesirable condition associated with the presence of a pathogenic antigenic molecule comprising the steps of (a) contacting a bispecific molecule with hematopoietic cells expressing a C3-like receptor, to form a hematopoietic cell/bispecific molecule complex; and (b) administering the hematopoietic cell/bispecific molecule complex to the mammal in a therapeutically effective amount.

The invention also provides a method of making a hematopoietic cell/bispecific molecule complex comprising contacting a bispecific molecule with hematopoietic cells that express a C3-like receptor under conditions conducive to binding, such that a complex forms, said complex consisting essentially of a hematopoietic cell bound to one or more bispecific molecules.

Taylor et al. (U.S. Pat. No. 5,879,679, hereinafter "the '679 patent") have demonstrated in some instances that the system saturates because the concentration of autoantibodies (or other pathogenic antigen) in the plasma is so high that even at the optimum input of bispecific antibodies, not all of the autoantibodies can be bound to the hematopoietic cells under standard conditions. For example, for a very high titer of autoantibody sera, a fraction of the autoantibody is not bound to the hematopoietic cells due to its high concentration.

However, saturation can be solved by using combinations of bispecific antibodies which contain monoclonal antibodies that bind to different sites on a C3-like receptor. For example, the monoclonal antibodies 7G9 and 1B4 bind to separate and non-competing sites on the primate C3 receptor. Therefore, a "cocktail" containing a mixture of two bispecific antibodies, each made with a different monoclonal antibody to the C3-like receptor, may give rise to greater binding of antibodies to red blood cells. The bispecific antibodies of the present invention can also be used in combination with certain fluids used for intravenous infusions.

In yet another embodiment, the bispecific molecule, such as a bispecific antibody, is prebound to red blood cells in vitro as described above, using a blend of at least two different bispecific antibodies. In this embodiment, the two different bispecific antibodies bind to the same antigen, but also bind to distinct and non-overlapping recognition sites on the C3-like receptor. By using at least two non-overlapping bispecific antibodies for binding to the C3-like receptor, the number of bispecific antibody-antigen complexes that can bind to a single red blood cell is increased. Thus, by allowing more than one bispecific antibody to bind to a single C3-like receptor, antigen clearance is enhanced, particularly in cases where the antigen is in very high concentrations (see for example the '679 patent, column 6, lines 41-64).

5.6. Kits

The invention also provides kits containing the intein antigen recognition portion fragments of the invention, or one or more nucleic acids encoding the intein antigen recognition portion fragments of the invention, or cells transformed with such nucleic acids, in one or more containers. The nucleic acids can be integrated into the chromosome, or exist as vectors (e.g., plasmids, particularly plasmid expression vectors). Kits containing the pharmaceutical compositions of the invention are also provided.

5.7. Protein Trans-splicing for Producing Other Bispecific Molecules

Although protein trans-splicing is useful in producing bispecific molecules that bind a C3-like receptor and an antigen, it will be recognized by one skilled in the art that other bispecific molecules can also be produced by protein trans-splicing. It is the intention that the production of such bispecific molecules is also within the scope of the present invention. As a non-limiting example, protein trans-splicing can be used for the production of bispecific molecules that comprise an antigen recognition portion that binds the transferrin receptor, such as but is not limited to an anti-transferrin receptor mAb, and an antigen recognition portion that binds an appropriate receptor in the brain, such as but is not limited to a peptide therapeutic molecule that binds the epidermal growth factor receptor in the brain. The anti-transferrin receptor mAb can undergo receptor-mediated transcytosis through the brain capillary endothelial wall which forms the blood-brain barrier (BBB). Therefore, the bispecific molecules are useful in the delivery to the brain drugs that are otherwise not transportable through BBB (see, for example, Deguchi et al., 1999, Bioconjugate Chem. 10:32-37; Li et al., 1999, Protein Engineering 12:787-796).

6. Example: Bispecific Molecule Comprising Anti-CR1 mAb X α-subunit of FcεRI for Removing IgE The following example describes the production of a bispecific molecule comprising an anti-CR1 mAb and the α-subunit of FcεRI. This example is a preferred embodiment of the invention.

IgE has been implicated in many allergic diseases. FcεRI is a human IgE receptor that plays an important role in the induction and maintenance of an allergic response (Saban et al., 1993, J. Allergy Clin. Immunol. 94:836-843; Turner et al., 1999, Nature 402:B24-B30; Chang, 2000, Nature Biotechnology 18:157-162). Of the three subunits that compose the FcεRI, i.e., the α-, β- and γ-subunits, the α-subunit binds the Fc portion of IgE. It has been found that the α-subunit of the FcεRI is sufficient for high affinity IgE binding, whereas the β- and γ-subunits do not play a critical role in IgE binding (Hakimi et al., J. Biol. Chem. 265:22079-22081). A bispecific molecule comprising an anti-CR1 mAb and the α-subunit of FcεRI is therefore useful in treating IgE-mediated diseases by removing IgE from the circulation.

Hybridoma cell line ATCC HB 8592 is obtained from the American Type Culture Collection (ATCC). Hybridomas are grown to log phase in Dulbecco's Modified Eagle's Medium (DMEM). Total RNA is isolated from $10^7$ hybridoma cells. The hybridoma cells are first washed in PBS. The cells are then resuspended in 1 ml buffer GTC (4M Guanidine-Isothiocyanate, 25 mM Sodium Citrate, 0.5% Sarcoyl, 0.1M b-mercaptoethanol). 0.1 ml sodium acetate (3M, pH 5.2), 0.5 ml phenol, and 0.2 ml choloroform are then added to the cell suspension. The cell suspension is then centrifuged at 10,000×g for 15 minutes. Supernatant is precipitated using 1 volume of isopropanol and is centrifuged at 10,000×g for 15 minutes. The pellet is washed in 70% EtOH and allowed air dry before is resuspended in 100 ml DEPC-treated water.

cDNA is prepared by adding 10 ml of RNA to a buffer comprising 5 ml 10× RT buffer (0.5 M Tris-HCl (pH 8.2), 0.1 M $MgCl_2$, and 1 M KCl), 5 ml DTT (100 mM), 5 ml dNTP (5 mM each), 1 ml oligonucleotides (10 pmols/ml each), 5 ml RNAsin (10 u/ml), 5 ml RTase (100 u/ml), and 14 ml $H_2O$ and incubating at 37° C. for 1 hour. The reaction mixture is then boiled for 3 minutes and quenched on ice.

PCR amplification is carried out using 5-10 ml cDNA in a buffer comprising 2.5 ml each forward and reverse primers (10 pmol/ml each) 5 ml 10× PCR buffer (0.1 M Tris-HCl (pH 8.3), 15 mM $MgCl_2$, and 0.5 M KCl), 2.5 ml dNTP (5 mM each), 0.5 ml BSA (10 mg/ml), and about 50 ml $H_2O$. The reaction mixture is overlaid with parafin oil and heated to 94° C. for 5 minutes in PCR block before 0.5 to 1 Taq DNA polymerase (5 u/ml) is added. 30 temperature cycles: 94° C. 1 minute, 60° C. 1 minute, 72° C. 2 minutes are used.

PCR products are purified by gel electrophoresis. Heavy and light chains.

The N-intein of the Ssp DnaE gene is amplified from plasmid pDnaE-C-209 with primers 5'-TTTGGTAC-CGAAATTTTAA-CCGTTGAG-3' (SEQ ID NO.: 5) and 5'-GGCTCTTCCTTTAAATTGTCCCAGCGTCAAG-3' (SEQ ID NO.: 6). The N-terminal splice junction sequence containing the 5 intein N-terminal residues and 5 native N-extein residues are ligated to the C-terminus of the amplified product.

The extended C-intein of the Ssp DnaE gene consisting the C-intein and a cysteine is prepared by peptide synthesis with N-(9-fluorenyl)methoxycarbonyl chemistry on an Applied Biosystems Model 431 peptide synthesizer using 4-methyl benzhydrylamine resin (Novabiochem), O-trityl-protected threonine, double coupling of all threonine and arginine residues, an acetic anhydride blocking step at each cycle, and N-methylpyrrolidone supplemented with dimethyl sulfoxide to 10%. The peptide is cleaved from the resin and deprotected with 6.25%(w/v) phenol in thioanisole:1,2-ethanedithiol:water:trifluoroacetic acid (2:1:2:20). The peptides are purified by HPLC (Rainin) using a preparative C8 column (Vydac).

The sequence of nucleic acid encoding the α-subunit of human FcεRI is given in Kochan et al., 1988, Nucleic Acids Research 16:3584 (Accession No. X06948).

The nucleic acid encoding the Ssp N-intein is fused to the nucleic acid encoding the heavy chain of the anti-CR1 mAb such that a fusion protein that consists of the N-terminus of the Ssp N-intein fused to the C-terminus of the heavy chain of the anti-CR1 mAb is encoded. Vectors containing the nucleic acid encoding the fusion polypeptide fragment and the nucleic acid encoding the light chain of the anti-CR1 mAb are constructed by operably linking the nucleic acids to the simian virus 40 regulatory elements according to Mulligan et al., 1980, Science 209:1423-1427. The two vectors are co-transfected into CHO cells according to Subramani et al. (Subramani et al., 1981, J. Mol. Cell. Biol. 1:854-864) for the production of N-intein anti-CR1 mAb.

DNA construct containing the α-subunit of human FcεRI is constructed according to Hakimi et al., 1990, J. Biol. Chem. 265:22079-22081. Nucleic acid encoding the Ssp C-intein is then fused to the DNA construct containing the α-subunit of human FcεRI. The DNA construct containing the Ssp C-intein fused to the α-subunit is transfected into CHO cells for production according to Haak-Frendscho et al., 1993, J. Immunol. 151:351-8.

The N-intein anti-CR1 fragment and the C-intein FcεRI α-subunit fragment are mixed in reaction buffer (100 mM Tris-HCl, pH 7.0, containing 500 mM NaCl). The final concentrations of the N-intein and C-intein fragments are both 500 mM. The mixture is allowed to react at room temperature overnight.

The bispecific molecules are purified by three-step successive affinity chromatography: the first column is made of protein A bound to a solid matrix, where the Fc portion of the antibody binds protein A, and wherein the antibodies bind the column; followed by a second column that utilizes CR1 binding to a solid matrix which assays for CR1 binding via the anti-CR1 mAb portion of the bispecific molecule; and followed by a third column that utilizes specific binding of IgE bound by the FceRI portion of the bispecific molecule.

The bispecific molecules can be characterized by SDS-PAGE and Western blot. The molecular weight of the bispecific molecule is determined by SDS-PAGE. The bispecificity of the molecules in the appropriate band is then determined by Western blots with both CR1 and the antigen of interest.

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of producing a bispecific molecule having a first antigen recognition portion that binds a C3b-like receptor and a second antigen recognition portion that binds a pathogenic antigenic molecule, comprising contacting an N-intein first antigen recognition portion and a C-intein second antigen recognition portion under conditions such that protein trans-splicing occurs, wherein said N-intein first antigen recognition portion comprises said first antigen recognition portion conjugated to the amino terminus of an N-intein of a split intein, and wherein said C-intein second antigen recognition portion comprises said second antigen recognition portion conjugated to the carboxy terminus of a C-intein containing a splice junction of said split intein, wherein the amino acid residue immediately at the C-terminal side of the splice junction of said C-intein is an amino acid residue selected from the group consisting of cysteine, serine, and threonine.

2. The method of claim 1, further comprising:

(a) obtaining said N-intein first antigen recognition portion by conjugating said first antigen recognition portion to the amino terminus of a molecule comprising said N-intein of a split intein before contacting an N-intein first antigen recognition portion and a C-intein second antigen recognition portion under conditions such that protein trans-splicing occurs; and (b) obtaining said C-intein second antigen recognition portion by conjugating said second antigen recognition portion to the carboxy terminus of a molecule comprising said C-intein of said split intein before contacting an N-intein first antigen recognition portion and a C-intein second antigen recognition portion under conditions such that protein trans-splicing occurs.

3. The method of claim 1 or 2, wherein said split intein is a naturally occurring split intein.

4. The method of claim 3, wherein the sequence of the N-intein of said split intein is SEQ ID NO:1, and the sequence of the C-intein of said split intein is SEQ ID NO:2.

5. The method of claim 1 or 2, wherein said split intein is an engineered split intein generated by separating a naturally occurring non-split intein into an amino terminal fragment and a carboxy terminal fragment such that said amino terminal fragment and said carboxy terminal fragment can reconstitute and undergo trans-splicing.

6. The method of claim 5, wherein said engineered split intein is generated from the *Mycobacterium tuberculosis* RecA intein.

7. The method of claim 1 or 2, wherein said N-intein further comprises a sequence of 1 or more native proximal N-extein amino acid residues attached to the amino terminus of the splice junction of said N-intein.

8. The method of claim 7, wherein said N-intein comprises a sequence of 3 to 5 native proximal N-extein amino acid residues attached to the amino terminus of the splice junction of said N-intein.

9. The method of claim 1 or 2, wherein said C-intein further comprises an amino acid residue selected from the group consisting of cysteine, serine, and threonine at the carboxy terminus of the splice junction.

10. The method of claim 9, wherein said C-intein further comprises a sequence of 1 or more native proximal C-extein amino acid residues attached to the carboxy terminus of the splice junction of said C-intein.

11. The method of claim 10, wherein said C-intein comprises a sequence of 3 to 5 native proximal C-extein amino acid residues attached to the carboxy terminus of the splice junction of said C-intein.

12. The method of claim 1 or 2, wherein said N-intein comprises an unnatural amino acid residue such that upon conversion of said unnatural amino acid residue into a normal amino acid residue by a suitable means said N-intein becomes functional for trans-splicing.

13. The method of claim 12, wherein said unnatural amino acid residue is O-(2-nitrobenzyl)serine, and said suitable means comprises irradiating using light having a wavelength in the range of 300-350 nm.

14. The method of claim 1 or 2, wherein said first antigen recognition portion comprises an antigen binding domain that binds a C3-like receptor on a mammalian blood cell and an effector domain that facilitates transfer of said pathogenic antigen molecule from said mammalian blood cell to a phagocytic cell.

15. The method of claim 1 or 2, wherein said first antigen recognition portion is an monoclonal antibody.

16. The method of claim 15, wherein said N-intein first antigen recognition portion is generated by conjugating the carboxy terminus of the heavy chain of said monoclonal antibody to said amino terminus of said N-intein.

17. The method of claim 15, wherein said N-intein first antigen recognition portion fragment is generated by conjugating the carboxy terminus of the light chain of said monoclonal antibody to the amino terminus of said N-intein.

18. The method of claim 15, wherein the heavy and light chains of said monoclonal antibody are recombinantly expressed using same vector.

19. The method of claim 15, wherein the heavy and light chains of said monoclonal antibody are recombinantly expressed using separate vectors.

20. The method of claim 19, wherein said heavy and light chains of said monoclonal antibody are recombinantly expressed in same cell.

21. The method of claim 19, wherein said heavy and light chains of said monoclonal antibody are recombinantly expressed in separate cells using separate vectors, and wherein said heavy and light chains are assembled into said monoclonal antibody in vitro.

22. The method of claim 1 or 2, wherein said first antigen recognition portion is an ScFv that binds a C3-like receptor fused to the N-terminus of an immunoglobulin Fc domain.

23. The method of claim 1 or 2, wherein said second antigen recognition portion comprises a polypeptide.

24. The method of claim 1 or 2, wherein said N-intein first antigen recognition portion is produced recombinantly.

25. The method of claim 1 or 2, wherein said C-intein second antigen recognition portion is produced recombinantly.

26. The method of claim 1 or 2, wherein said C-intein second antigen recognition portion is produced by peptide synthesis.

27. The method of claim 1 or 2, wherein said N-intein first antigen recognition portion and said C-intein second antigen recognition portion are recombinantly co-expressed in a cell, and wherein said N-intein first antigen recognition portion and said C-intein second antigen recognition portion reconstitute and undergo trans-splicing in said cell to produce said bispecific molecule.

28. The method of claim 27, wherein said N-intein first antigen recognition portion and said C-intein second antigen recognition portion are expressed by separate expression vectors.

29. The method of claim 27, wherein said N-intein first antigen recognition portion and said C-intein second antigen recognition portion are expressed by one expression vector.

30. The method of claim 1 or 2, wherein said N-intein first antigen recognition portion is recombinantly expressed in a first cell and said C-intein second antigen recognition portion is recombinantly expressed in a second cell, and wherein said N-intein first antigen recognition portion and said C-intein second antigen recognition portion are mixed in vitro to produce said bispecific molecule.

* * * * *

SEQUENCE LISTING

```
<160> NUMBER OF SEQ ID NOS: 6

<210> SEQ ID NO 1
<211> LENGTH: 123
<212> TYPE: PRT
<213> ORGANISM: Synechocystis sp.

<400> SEQUENCE: 1

Cys Leu Ser Phe Gly Thr Glu Ile Leu Thr Val Glu Tyr Gly Pro Leu
1               5                   10                  15

Pro Ile Gly Lys Ile Val Ser Glu Glu Ile Asn Cys Ser Val Tyr Ser
            20                  25                  30

Val Asp Pro Glu Gly Arg Val Tyr Thr Gln Ala Ile Ala Gln Trp His
        35                  40                  45

Asp Arg Gly Glu Gln Glu Val Leu Glu Tyr Glu Leu Glu Asp Gly Ser
    50                  55                  60

Val Ile Arg Ala Thr Ser Asp His Arg Phe Leu Thr Thr Asp Tyr Gln
65                  70                  75                  80

Leu Leu Ala Ile Glu Glu Ile Phe Ala Arg Gln Leu Asp Leu Leu Thr
                85                  90                  95

Leu Glu Asn Ile Lys Gln Thr Glu Glu Ala Leu Asp Asn His Arg Leu
            100                 105                 110

Pro Phe Pro Leu Leu Asp Ala Gly Thr Ile Lys
        115                 120

<210> SEQ ID NO 2
<211> LENGTH: 37
<212> TYPE: PRT
<213> ORGANISM: Synechocystis sp.

<400> SEQUENCE: 2

Met Val Lys Val Ile Gly Arg Arg Ser Leu Gly Val Gln Arg Ile Phe
1               5                   10                  15
```

```
Asp Ile Gly Leu Pro Gln Asp His Asn Phe Leu Leu Ala Asn Gly Ala
            20                  25                  30

Ile Ala Ala Asn Cys
        35

<210> SEQ ID NO 3
<211> LENGTH: 10
<212> TYPE: PRT
<213> ORGANISM: Synechocystis sp.

<400> SEQUENCE: 3

Phe Asp Gln Met Val Lys Phe Ala Glu Tyr
1               5                   10

<210> SEQ ID NO 4
<211> LENGTH: 10
<212> TYPE: PRT
<213> ORGANISM: Synechocystis sp.

<400> SEQUENCE: 4

Cys Phe Asn Lys Ser His Ser Thr Ala Tyr
1               5                   10

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 5
tttggtaccg aaattttaac cgttgag                                      27

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 6
ggctcttcct ttaaattgtc ccagcgtcaa g                                 31
```